(12) United States Patent
Reddy et al.

(10) Patent No.: US 8,969,556 B2
(45) Date of Patent: Mar. 3, 2015

(54) PURINE-BASED TRIAZOLES

(75) Inventors: Prakash V. Reddy, Rolla, MO (US); Nanditha G. Nair, Alhambra, CA (US); Mark A. Smith, Chagrin Falls, OH (US); Gemma Casadesus, legal representative, Chagrin Falls, OH (US); Wataru Kudo, Cleveland Heights, OH (US)

(73) Assignee: Case Western Reserve University, Cleveland, OH (US)

( * ) Notice: Subject to any disclaimer, the term of this patent is extended or adjusted under 35 U.S.C. 154(b) by 42 days.

(21) Appl. No.: 13/879,101

(22) PCT Filed: Oct. 12, 2011

(86) PCT No.: PCT/US2011/055962
§ 371 (c)(1),
(2), (4) Date: Sep. 20, 2013

(87) PCT Pub. No.: WO2012/051296
PCT Pub. Date: Apr. 19, 2012

(65) Prior Publication Data
US 2014/0045866 A1     Feb. 13, 2014

Related U.S. Application Data

(60) Provisional application No. 61/392,237, filed on Oct. 12, 2010.

(51) Int. Cl.
*C07D 473/40* (2006.01)
*C07D 473/34* (2006.01)
*A61K 31/522* (2006.01)
*A61K 31/52* (2006.01)

(52) U.S. Cl.
CPC ............ *C07D 473/40* (2013.01); *C07D 473/34* (2013.01); *A61K 31/52* (2013.01)
USPC .......................... 544/277; 435/375; 514/263.3

(58) Field of Classification Search
USPC ........................................ 544/277; 514/263.3
See application file for complete search history.

(56) References Cited

U.S. PATENT DOCUMENTS

| | | | |
|---|---|---|---|
| 5,733,920 A | 3/1998 | Mansuri et al. | |
| 5,866,702 A * | 2/1999 | Mackman et al. | 544/277 |
| 2008/0096903 A1 | 4/2008 | Chen et al. | |
| 2011/0251172 A1 * | 10/2011 | Rivkin et al. | 514/210.18 |

FOREIGN PATENT DOCUMENTS

WO    WO 2010/014744    *  4/2010

OTHER PUBLICATIONS

Yi Chen, et al., "A Novel Rearrangmeent of fluorescent Thymidylate Synthase Inhibitor Analogues in ESI Tandem Spectrometry", Journal of the American Society for Mass Spectrometry. Mar. 21, 2010, 21(3), p. 403-410.

* cited by examiner

*Primary Examiner* — Shirley V Gembeh
(74) *Attorney, Agent, or Firm* — Tarolli, Sundheim, Covell & Tummino LLP

(57) ABSTRACT

A pharmaceutical composition for inhibiting at least protein kinase in a cell of a subject includes a purine based triazole.

11 Claims, 4 Drawing Sheets

D1 = Compound 6
D2 = Compound 7
D3 = Compound 9
D4 = Compound 8
Flav = Flavopiridol
Ros = Roscovitine Dose 1 μM D1 = Compound 6
D2 = Compound 7
D3 = Compound 9
D4 = Compound 8
Flav = Flavopiridol
Ros = Roscovitine

PURINE-BASED TRIAZOLES

RELATED APPLICATION

This application is a National Phase filing of PCT/US2011/055962, filed Oct. 12, 2011, which claims priority from U.S. Provisional Application No. 61/392,237, filed Oct. 12, 2010, the subject matter of which are incorporated herein by reference in their entirety.

TECHNICAL FIELD

This application relates to purine-based triazoles and to the use of the purine-based triazoles as protein kinase inhibitors and to treat diseases or disorders associated with protein kinases.

BACKGROUND OF THE INVENTION

Initiation, progression, and completion of the mammalian cell cycle are regulated by various cyclin-dependent kinase (CDK) complexes, which are critical for cell growth. CDKs are highly conserved among eukaryotic species. Higher eukaryotic cells contain several isoforms of CDKs that become activated in specific phases of the cell cycle. CDKs consist of a catalytic subunit, the prototype of which is CDC2, and a regulatory subunit (cyclin). Six human CDK proteins have been described so far (see, Meyerson, M., et al. (1992), EMBO J., 11:2909-2917; Meyerson, M., et al. (1994), Mol. Cell. Biol., 14:2077-2086; and Van den Heuvel, S., et al. (1993), Science, 262:2050-2054), namely, CDK1 (also known as CDC2) and CDK2-6. With the exception of CDK3, for which the regulatory cyclin has not yet been identified, all these CDK proteins are regulated by the transient association with one member of the cyclin family, i.e., cyclin A (CDC2, CDK2), B1-B3 (CDC2), D1-D3 (CDK2, CDK4, CDK5, CDK6), E (CDK2). Each step of the cell cycle is thought to be regulated by such CDK complexes: G1/S transition (CDK2/cyclin E, CDK3/unknown cyclin, CDK4/cyclin D1-D3, CDK6/cyclin D3), S phase (CDK2/cyclin A), G2 (CDC2/cyclin A), G2/M transition (CDC2/cyclins B).

The function of CDKs is to phosphorylate and thus activate or deactivate certain proteins, including e.g., retinoblastoma proteins, lamins, histone H1, and components of the mitotic spindle. The catalytic step mediated by CDKs involves a phospho-transfer reaction from ATP to the macromolecular enzyme substrate. Several groups of compounds (reviewed in e.g., Fischer, P. M. Curr. Opin. Drug Discovery Dev. 2001, 4, 623-634) have been found to possess anti-proliferative properties by virtue of CDK-specific ATP antagonism.

WO 98/05335 discloses 2,6,9-trisubstituted purine derivatives that are selective inhibitors of cell cycle kinases. Such compounds are useful in the treatment of autoimmune disorders, e.g., rheumatoid arthritis, lupus, type I diabetes, multiple sclerosis; treating cancer, cardiovascular disease, such as restenosis, host v graft disease, gout, polycystic kidney disease and other proliferative diseases whose pathogenesis involves abnormal cell proliferation.

WO 99/07705 discloses purine analogues that inhibit inter alia protein kinases, G-proteins and polymerases. More specifically, WO '705 discloses methods of using such purine analogues to treat cellular proliferative disorders and neurodegenerative diseases.

WO 97/20842 also discloses purine derivatives displaying antiproliferative properties, which are useful in treating cancer, psoriasis, and neurodegenerative disorders.

SUMMARY OF THE INVENTION

This application relates to substituted purine-based triazoles that can inhibit protein kinases, such as cyclin-dependent kinase (CDK), G proteins and polymerases, as well as pharmaceutical compositions comprising the same, and methods for formulating or using the same to treat diseases or disorders associated with protein kinases, G proteins and plymerases.

In one embodiment, the substituted purine-based analog can include the following formula (I):

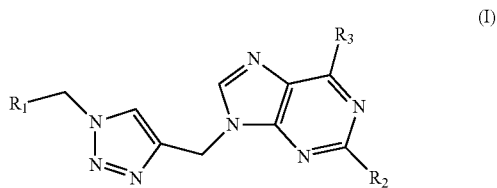

or a pharmaceutically acceptable salt thereof, wherein
where $R_1$ is a hydrophobic, substituted or unsubstituted, aryl, cyclic, or heterocyclic group;
where $R_2$ and $R_3$ independently represent substituents selected from the group consisting of hydrogen, halogen atom, $C_1$-$C_{24}$ alkyl, $C_2$-$C_{24}$ alkenyl, $C_2$-$C_{24}$ alkynyl, $C_3$-$C_{20}$ aryl, $C_6$-$C_{24}$ alkaryl, $C_6$-$C_{24}$ aralkyl, silyl, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, $C_2$-$C_{24}$ alkylcarbonyl (—CO-alkyl), $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—NH$_2$), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_1$-$C_{24}$ alkyl)$_2$), mono-substituted arylcarbamoyl (—(CO)—NH-aryl), thiocarbamoyl (—(CS)—NH$_2$), carbamido (—NH—(CO)—NH$_2$), cyano (—CN), isocyano (—NC), cyanato (—O—CN), isocyanato (ONC), isothiocyanato (—S—CN), azido (—N=N$^+$=N$^-$), formyl (—(CO)—H), thioformyl (—(CS)—H), amino (—NH$_2$), mono- and di-($C_1$-$C_{24}$ alkyl)-substituted amino, mono- and di-($C_5$-$C_{20}$ aryl)-substituted amino, $C_2$-$C_{24}$ alkylamido (—NH—(CO)-alkyl), $C_6$-$C_{20}$ arylamido (—NH—(CO)-aryl), imino, alkylimino, arylimino, nitro (—NO$_2$), nitroso (—NO), sulfonic acid (—SO$_2$.OH), sulfonato (—SO$_2$—O$^-$), $C_1$-$C_{24}$ alkylsulfanyl (—S-alkyl), arylsulfanyl, $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), phosphono (—P(O)(OH)$_2$), phosphonato (—P(O)(O—)$_2$), phosphinato (—P(O)(O$^-$)), phospho (—PO$_2$), and phosphino (—PH$_2$), and where each $R_2$ and $R_3$ being independently unsubstituted or substituted where appropriate by one or more —OH, halogen, amino or alkyl groups.

In some embodiments, $R_1$ is a fluorinated aryl, cyclic, or heterocyclic group. In other embodiments $R_2$ and $R_3$ are each independently a halogen atom, $C_1$-$C_{24}$ alkyl, $C_2$-$C_{24}$ alkenyl, $C_2$-$C_{24}$ alkynyl, $C_3$-$C_{20}$ aryl, $C_6$-$C_{24}$ alkaryl, $C_6$-$C_{24}$ aralkyl, or an $R_4$—NH—, $R_4$—NH—NH—, NH$_2$—R'—NH— or $R_4$—NH—R'—NH— radical, in which $R_4$ represents a straight- or branched-chain, saturated or unsaturated alkyl radical, an aryl or cycloalkyl radical or a heterocyclic ring and R' represents a straight- or branched-chain, saturated or unsaturated alkylene group or an arylene or cycloalkylene group, where $R_4$ and R' each contain 1 to 8 carbon atoms, and where each $R_2$ and $R_3$ can be independently unsubstituted or substituted, where appropriate, by one or more —OH, halogen, amino or alkyl groups.

Another embodiment of the application relates to a method of inhibiting a protein selected from the group consisting of protein kinases, G proteins and polymerases by contacting the protein with a substituted purine-based triazole. In some embodiments, the protein is a protein kinase. In other embodiments, the protein kinase is a cyclin-dependent kinase. In still other embodiments, the cyclin-dependent kinase is a member selected from the group consisting of CDK1 (CDC2), CDK2, CDK3, CDK4, CDK5, CDK6, CDK7 and CDK8 and, in particular CDK5.

Yet another embodiment of the application relates to the use of the substituted purine-based triazole in treating a disease process featuring abnormal cell cycle or cellular proliferation, including, but not limited to, abnormal stimulation of endothelial cells (e.g., atherosclerosis), neoplastic disorders, solid tumors and tumor metastasis, benign tumors, for example, hemangiomas, acoustic neuromas, neurofibromas, trachomas, and pyogenic granulomas, cancer, vascular malfunctions, abnormal wound healing, inflammatory and immune disorders, Bechet's disease, gout or gouty arthritis, abnormal angiogenesis accompanying, for example, rheumatoid arthritis, psoriasis, diabetic retinopathy, other ocular angiogenic diseases, such as retinopathy of prematurity (retrolental fibroplastic), macular degeneration, corneal graft rejection, neuroscular glaucoma and Oster Webber syndrome, alopecia, fungal, parasitic and viral infections, such as cytomegaloviral infections, neurological disorders, stroke neurofibromatosis, endotoxic shock, hypertrophic scar formation, inflammatory bowel disease, transplant rejection, vascular smooth muscle cell proliferation associated with atherosclerosis, pulmonary fibrosis, arthritis, glomerulonephritis, restenosis following angioplasty or vascular surgery, and other post-surgical stenosis and restenosis.

In some embodiments, the disease or disorder treated by the substituted purine-based triazole is a neurological disorder. In other embodiments, the disease or disorder treated by the substituted purine-based triazole is a neoplastic disorder.

BRIEF DESCRIPTION OF THE DRAWINGS

The foregoing and other features of the application will become apparent to those skilled in the art to which the application relates upon reading the following description with reference to the accompanying drawings, in which.

DETAILED DESCRIPTION

Figure 1:
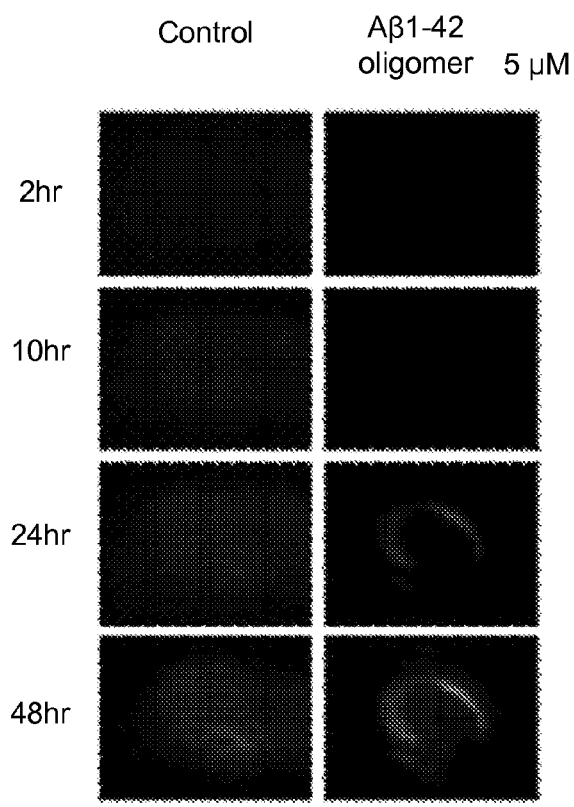
FIG. 1 illustrates fluorescence microscopy images showing the time-dependent PI uptake in hippocampal slices exposed to 5 μM oligomers.

For convenience, certain terms employed in the specification, examples, and appended claims are collected here. Unless defined otherwise, all technical and scientific terms used herein have the same meaning as commonly understood by one of ordinary skill in the art to which this application belongs.

The articles "a" and "an" are used herein to refer to one or to more than one (i.e., to at least one) of the grammatical object of the article. By way of example, "an element" means one element or more than one element.

The terms "comprise," "comprising," "include," "including," "have," and "having" are used in the inclusive, open sense, meaning that additional elements may be included. The terms "such as", "e.g.,", as used herein are non-limiting and are for illustrative purposes only. "Including" and "including but not limited to" are used interchangeably.

The term "or" as used herein should be understood to mean "and/or", unless the context clearly indicates otherwise.

It will be noted that the structure of some of the compounds of the application include asymmetric (chiral) carbon atoms. It is to be understood accordingly that the isomers arising from such asymmetry are included within the scope of the invention, unless indicated otherwise. Such isomers can be obtained in substantially pure form by classical separation techniques and by stereochemically controlled synthesis. The compounds of this application may exist in stereoisomeric form, therefore can be produced as individual stereoisomers or as mixtures.

"Isomerism" means compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four nonidentical substituents is termed a "chiral center".

"Chiral isomer" means a compound with at least one chiral center. It has two enantiomeric forms of opposite chirality and may exist either as an individual enantiomer or as a mixture of enantiomers. A mixture containing equal amounts of individual enantiomeric forms of opposite chirality is termed a "racemic mixture". A compound that has more than one chiral center has 2n-1 enantiomeric pairs, where n is the number of chiral centers. Compounds with more than one chiral center may exist as either an individual diastereomer or as a mixture of diastereomers, termed a "diastereomeric mixture". When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the Sequence Rule of Cahn, Ingold and Prelog. (Cahn et al, Angew. Chem. Inter. Edit.

1966, 5, 385; errata 511; Cahn et al., Angew. Chem. 1966, 78, 413; Cahn and Ingold, J Chem. Soc. 1951 (London), 612; Cahn et al., Experientia 1956, 12, 81; Cahn, J., Chem. Educ. 1964, 41, 116).

"Geometric Isomers" means the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules.

Further, the structures and other compounds discussed in this application include all atropic isomers thereof. "Atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

The terms "crystal polymorphs" or "polymorphs" or "crystal forms" means crystal structures in which a compound (or salt or solvate thereof) can crystallize in different crystal packing arrangements, all of which have the same elemental composition. Different crystal forms usually have different X-ray diffraction patterns, infrared spectra, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions.

As defined herein, the term "derivative", refers to compounds that have a common core structure, and are substituted with various groups as described herein. For example, all of the compounds represented by formula I are purine-based triazoles and have formula I as a common core.

The term "bioisostere" refers to a compound resulting from the exchange of an atom or of a group of atoms with another, broadly similar, atom or group of atoms. The objective of a bioisosteric replacement is to create a new compound with similar biological properties to the parent compound. The bioisosteric replacement may be physicochemically or topologically based. Examples of carboxylic acid bioisosteres include acyl sulfonimides, tetrazoles, sulfonates, and phosphonates. See, e.g., Patani and LaVoie, Chem. Rev. 96, 3147-3176 (1996).

The phrases "parenteral administration" and "administered parenterally" are art-recognized terms, and include modes of administration other than enteral and topical administration, such as injections, and include, without limitation, intravenous, intramuscular, intrapleural, intravascular, intrapericardial, intraarterial, intrathecal, intracapsular, intraorbital, intracardiac, intradermal, intraperitoneal, transtracheal, subcutaneous, subcuticular, intra-articular, subcapsular, subarachnoid, intraspinal and intrastemal injection and infusion.

The term "treating" is art-recognized and includes inhibiting a disease, disorder or condition in a subject, e.g., impeding its progress; and relieving the disease, disorder or condition, e.g., causing regression of the disease, disorder and/or condition. Treating the disease or condition includes ameliorating at least one symptom of the particular disease or condition, even if the underlying pathophysiology is not affected.

The term "preventing" is art-recognized and includes stopping a disease, disorder or condition from occurring in a subject, which may be predisposed to the disease, disorder and/or condition but has not yet been diagnosed as having it. Preventing a condition related to a disease includes stopping the condition from occurring after the disease has been diagnosed but before the condition has been diagnosed.

A "pharmaceutical composition" is a formulation containing the disclosed compounds in a form suitable for administration to a subject. In a preferred embodiment, the pharmaceutical composition is in bulk or in unit dosage form. The unit dosage form is any of a variety of forms, including, for example, a capsule, an IV bag, a tablet, a single pump on an aerosol inhaler, or a vial. The quantity of active ingredient (e.g., a formulation of the disclosed compound or salts thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, intranasal, and the like. Dosage forms for the topical or transdermal administration of a compound of this invention include powders, sprays, ointments, pastes, creams, lotions, gels, solutions, patches and inhalants. In a preferred embodiment, the active compound is mixed under sterile conditions with a pharmaceutically acceptable carrier, and with any preservatives, buffers, or propellants that are required.

The term "flash dose" refers to compound formulations that are rapidly dispersing dosage forms.

The term "immediate release" is defined as a release of compound from a dosage form in a relatively brief period of time, generally up to about 60 minutes. The term "modified release" is defined to include delayed release, extended release, and pulsed release. The term "pulsed release" is defined as a series of releases of drug from a dosage form. The term "sustained release" or "extended release" is defined as continuous release of a compound from a dosage form over a prolonged period.

The phrase "pharmaceutically acceptable" is art-recognized. In certain embodiments, the term includes compositions, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" is art-recognized, and includes, for example, pharmaceutically acceptable materials, compositions or vehicles, such as a liquid or solid filler, diluent, excipient, solvent or encapsulating material, involved in carrying or transporting any subject composition from one organ, or portion of the body, to another organ, or portion of the body. Each carrier must be "acceptable" in the sense of being compatible with the other ingredients of a subject composition and not injurious to the patient. In certain embodiments, a pharmaceutically acceptable carrier is non-pyrogenic. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, sunflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The compounds of the application are capable of further forming salts. All of these forms are also contemplated within the scope of the claimed invention.

"Pharmaceutically acceptable salt" of a compound means a salt that is pharmaceutically acceptable and that possesses the desired pharmacological activity of the parent compound.

For example, the salt can be an acid addition salt. One embodiment of an acid addition salt is a hydrochloride salt The pharmaceutically acceptable salts can be synthesized from a parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of salts are found in Remington's Pharmaceutical Sciences, 18th ed. (Mack Publishing Company, 1990). For example, salts can include, but are not limited to, the hydrochloride and acetate salts of the aliphatic amine-containing, hydroxyl amine-containing, and imine-containing compounds of the present invention.

It should be understood that all references to pharmaceutically acceptable salts include solvent addition forms (solvates) or crystal forms (polymorphs) as defined herein, of the same salt.

The compounds described herein can also be prepared as esters, for example pharmaceutically acceptable esters. For example, a carboxylic acid function group in a compound can be converted to its corresponding ester, e.g., a methyl, ethyl, or other ester. Also, an alcohol group in a compound can be converted to its corresponding ester, e.g., an acetate, propionate, or other ester.

The compounds described herein can also be prepared as prodrugs, for example pharmaceutically acceptable prodrugs. The terms "pro-drug" and "prodrug" are used interchangeably herein and refer to any compound, which releases an active parent drug in vivo. Since prodrugs are known to enhance numerous desirable qualities of pharmaceuticals (e.g., solubility, bioavailability, manufacturing, etc.) the compounds of the present invention can be delivered in prodrug form. Thus, the present invention is intended to cover prodrugs of the presently claimed compounds, methods of delivering the same and compositions containing the same. "Prodrugs" are intended to include any covalently bonded carriers that release an active parent drug of the present invention in vivo when such prodrug is administered to a subject. Prodrugs of the present invention are prepared by modifying functional groups present in the compound in such a way that the modifications are cleaved, either in routine manipulation or in vivo, to the parent compound. Prodrugs include compounds of the present invention wherein a hydroxy, amino, sulfhydryl, carboxy, or carbonyl group is bonded to any group that may be cleaved in vivo to form a free hydroxyl, free amino, free sulftydryl, free carboxy or free carbonyl group, respectively.

Examples of prodrugs include, but are not limited to, esters (e.g., acetate, dialkylaminoacetates, formates, phosphates, sulfates, and benzoate derivatives) and carbamates (e.g., N,N-dimethylaminocarbonyl) of hydroxy functional groups, ester groups (e.g., ethyl esters, morpholinoethanol esters) of carboxyl functional groups, N-acyl derivatives (e.g., N-acetyl) N-Mannich bases, Schiff bases and enamines of amino functional groups, oximes, acetals, ketals and enol esters of ketone and aldehyde functional groups in compounds of Formula I, and the like, See Bundegaard, H. "Design of Prodrugs" p1-92, Elesevier, New York-Oxford (1985).

"Protecting group" refers to a grouping of atoms that when attached to a reactive group in a molecule masks, reduces or prevents that reactivity. Examples of protecting groups can be found in Green and Wuts, Protective Groups in Organic Chemistry, (Wiley, 2.sup.nd ed. 1991); Harrison and Harrison et al., Compendium of Synthetic Organic Methods, Vols. 1-8 (John Wiley and Sons, 1971-1996); and Kocienski, Protecting Groups, (Verlag, 3.sup.rd ed. 2003).

Representative hydroxy protecting groups include those where the hydroxy group is either acylated or alkylated such as benzyl, and trityl ethers as well as alkyl ethers, tetrahydropyranyl ethers, trialkylsilyl ethers and allyl ethers.

Additionally, the salts of the compounds described herein, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

"Solvates" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

The compounds, salts and prodrugs described herein can exist in several tautomeric forms, including the enol and imine form, and the keto and enamine form and geometric isomers and mixtures thereof. All such tautomeric forms are included within the scope of the present invention. Tautomers exist as mixtures of a tautomeric set in solution. In solid form, usually one tautomer predominates. Even though one tautomer may be described, the present application includes all tautomers of the present compounds. A tautomer is one of two or more structural isomers that exist in equilibrium and are readily converted from one isomeric form to another. This reaction results in the formal migration of a hydrogen atom accompanied by a switch of adjacent conjugated double bonds. In solutions where tautomerization is possible, a chemical equilibrium of the tautomers will be reached. The exact ratio of the tautomers depends on several factors, including temperature, solvent, and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs.

Tautomerizations can be catalyzed by: Base: 1. deprotonation; 2. formation of a delocalized anion (e.g., an enolate); 3. protonation at a different position of the anion; Acid: 1. protonation; 2. formation of a delocalized cation; 3. deprotonation at a different position adjacent to the cation.

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar or comparable in function and appearance, but not in structure or origin to the reference compound.

A "patient," "subject," or "host" to be treated by the subject method may mean either a human or non-human animal, such as primates, mammals, and vertebrates.

The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic, i.e., it protects the host against developing the unwanted condition, whereas if it is administered after manifestation of the unwanted condition, the treatment is therapeutic (i.e., it is intended to diminish, ameliorate, or stabilize the existing unwanted condition or side effects thereof).

The terms "therapeutic agent", "drug", "medicament" and "bioactive substance" are art-recognized and include molecules and other agents that are biologically, physiologically, or pharmacologically active substances that act locally or systemically in a patient or subject to treat a disease or condition. The terms include without limitation pharmaceutically acceptable salts thereof and prodrugs. Such agents may be acidic, basic, or salts; they may be neutral molecules, polar molecules, or molecular complexes capable of hydrogen bonding; they may be prodrugs in the form of ethers, esters, amides and the like that are biologically activated when administered into a patient or subject.

The phrase "therapeutically effective amount" is an art-recognized term. In certain embodiments, the term refers to an amount of a therapeutic agent that, when incorporated into a polymer, produces some desired effect at a reasonable benefit/risk ratio applicable to any medical treatment. In certain embodiments, the term refers to that amount necessary or sufficient to eliminate, reduce or maintain a target of a particular therapeutic regimen. The effective amount may vary depending on such factors as the disease or condition being treated, the particular targeted constructs being administered, the size of the subject or the severity of the disease or condition. One of ordinary skill in the art may empirically determine the effective amount of a particular compound without necessitating undue experimentation. In certain embodiments, a therapeutically effective amount of a therapeutic agent for in vivo use will likely depend on a number of factors, including: the rate of release of an agent from a polymer matrix, which will depend in part on the chemical and physical characteristics of the polymer; the identity of the agent; the mode and method of administration; and any other materials incorporated in the polymer matrix in addition to the agent.

The term "ED50" is art-recognized. In certain embodiments, ED50 means the dose of a drug, which produces 50% of its maximum response or effect, or alternatively, the dose, which produces a pre-determined response in 50% of test subjects or preparations. The term "LD50" is art-recognized. In certain embodiments, LD50 means the dose of a drug, which is lethal in 50% of test subjects. The term "therapeutic index" is an art-recognized term, which refers to the therapeutic index of a drug, defined as LD50/ED50.

The term "substituted," as used herein, means that any one or more hydrogens on the designated atom is replaced with a selection from the indicated group, provided that the designated atom's normal valency is not exceeded, and that the substitution results in a stable compound. When the substituent is keto (i.e., =O), then 2 hydrogens on the atom are replaced. Ring double bonds, as used herein, are double bonds that are formed between two adjacent ring atoms (e.g., C=C, C=N, or N=N).

With respect to any chemical compounds, the present application is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

When a bond to a substituent is shown to cross a bond connecting two atoms in a ring, then such substituent can be bonded to any atom in the ring. When a substituent is listed without indicating the atom via which such substituent is bonded to the rest of the compound of a given formula, then such substituent can be bonded via any atom in such substituent. Combinations of substituents and/or variables are permissible, but only if such combinations result in stable compounds.

When an atom or a chemical moiety is preceded or followed by a subscripted numeric range (e.g., $C_{1-6}$), the invention is meant to encompass each number within the range as well as all intermediate ranges. For example, "$C_{1-6}$ alkyl" or is meant to include alkyl groups with 1, 2, 3, 4, 5, 6, 1-6, 1-5, 1-4, 1-3, 1-2, 2-6, 2-5, 2-4, 2-3, 3-6, 3-5, 3-4, 4-6, 4-5, and 5-6 carbons.

As used herein, "alkyl" is intended to include both branched (e.g., isopropyl, tert-butyl, isobutyl), straight-chain e.g., methyl, ethyl, propyl, butyl, pentyl, hexyl, heptyl, octyl, nonyl, decyl), and cycloalkyl (e.g., alicyclic) groups (e.g., cyclopropyl, cyclopentyl, cyclohexyl, cycloheptyl, cyclooctyl), alkyl substituted cycloalkyl groups, and cycloalkyl substituted alkyl groups. Such aliphatic hydrocarbon groups have a specified number of carbon atoms. For example, $C_{1-6}$ alkyl is intended to include $C_1$, $C_2$, $C_3$, $C_4$, $C_5$, and $C_6$ alkyl groups. As used herein, "lower alkyl" refers to alkyl groups having from 1 to 6 carbon atoms in the backbone of the carbon chain. "Alkyl" further includes alkyl groups that have oxygen, nitrogen, sulfur or phosphorous atoms replacing one or more hydrocarbon backbone carbon atoms. In certain embodiments, a straight chain or branched chain alkyl has six or fewer carbon atoms in its backbone (e.g., $C_1$-$C_6$ for straight chain, $C_3$-$C_6$ for branched chain), for example four or fewer. Likewise, certain cycloalkyls have from three to eight carbon atoms in their ring structure, such as five or six carbons in the ring structure.

The term "substituted alkyls" refers to alkyl moieties having substituents replacing a hydrogen on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "aralkyl" moiety is an alkyl substituted with an aryl (e.g., phenylmethyl (benzyl)).

As used herein, "alkenyl" is intended to include hydrocarbon chains of either straight or branched configuration having one or more carbon-carbon double bonds occurring at any stable point along the chain. For example, $C_{2-6}$ alkenyl is intended to include $C_2$, $C_3$, $C_4$, $C_5$, and $C_6$ alkenyl groups. Examples of alkenyl include, but are not limited to, ethenyl and propenyl.

As used herein, "alkynyl" is intended to include hydrocarbon chains of either straight or branched configuration having one or more carbon-carbon triple bonds occurring at any stable point along the chain. For example, $C_{2-6}$ alkynyl is intended to include $C_2$, $C_3$, $C_4$, $C_5$, and $C_6$ alkynyl groups. Examples of alkynyl include, but are not limited to, ethynyl and propynyl.

Furthermore, "alkyl", "alkenyl", and "alkynyl" are intended to include moieties which are diradicals, i.e., having two points of attachment. A nonlimiting example of such an alkyl moiety that is a diradical is —$CH_2CH_2$—, i.e., a $C_2$ alkyl group that is covalently bonded via each terminal carbon atom to the remainder of the molecule.

"Aryl" includes groups with aromaticity, including 5- and 6-membered "unconjugated", or single-ring, aromatic groups that may include from zero to four heteroatoms, as well as "conjugated", or multicyclic, systems with at least one aromatic ring. Examples of aryl groups include benzene, substituted phenyl, pyrrole, furan, thiophene, thiazole, isothiazole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, or indolizine. Those aryl groups having heteroatoms in the ring structure may also be referred to as "aryl heterocycles", "heterocycles," "heteroaryls" or "heteroaromatics". The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, cyano, amino (including alkylamino, dialkylamino, arylamino, diarylamino, and alkylaryl amino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings, which are not aromatic so as to form a multicyclic system (e.g., tetralin, methylenedioxyphenyl).

The terms "heterocyclyl" or "heterocyclic group" include closed ring structures, e.g., 3- to 10-, or 4- to 7-membered rings, which include one or more heteroatoms. "Heteroatom" includes atoms of any element other than carbon or hydrogen. Examples of heteroatoms include nitrogen, oxygen, sulfur and phosphorus.

Heterocyclyl groups can be saturated or unsaturated and include pyrrolidine, oxolane, thiolane, piperidine, piperazine, morpholine, lactones, lactams such as azetidinones and pyrrolidinones, sultams, and sultones. Heterocyclic groups such as pyrrole and furan can have aromatic character. They include fused ring structures such as quinoline and isoquinoline. Other examples of heterocyclic groups include pyridine and purine. The heterocyclic ring can be substituted at one or more positions with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, or an aromatic or heteroaromatic moiety. Heterocyclic groups can also be substituted at one or more constituent atoms with, for example, a lower alkyl, a lower alkenyl, a lower alkoxy, a lower alkylthio, a lower alkylamino, a lower alkylcarboxyl, a nitro, a hydroxyl, —$CF_3$, or —CN, or the like.

As used herein, "halo" or "halogen" refers to fluoro, chloro, bromo, and iodo. "Counterion" is used to represent a small, negatively charged species such as fluoride, chloride, bromide, iodide, hydroxide, acetate, and sulfate.

"Stable compound" and "stable structure" are meant to indicate a compound that is sufficiently robust to survive isolation, and as appropriate, purification from a reaction mixture, and formulation into an efficacious therapeutic agent.

"Free compound" is used herein to describe a compound in the unbound state.

"Extinction coefficient" is a constant used in the Beer-Lambert Law which relates the concentration of the substance being measured (in moles) to the absorbance of the substance in solution (how well the substance in solution blocks light beamed through it from getting out on the other side). It is an indicator of how much light a compound absorbs at a particular wavelength.

In the specification, the singular forms also include the plural, unless the context clearly dictates otherwise. Unless defined otherwise, all technical and scientific terms used herein have the same meaning as commonly understood by one of ordinary skill in the art to which this invention belongs. In the case of conflict, the present specification will control.

Throughout the description, where compositions are described as having, including, or comprising, specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the invention remains operable. Moreover, two or more steps or actions can be conducted simultaneously.

"Small molecule" is an art-recognized term. In certain embodiments, this term refers to a molecule, which has a molecular weight of less than about 2000 amu, or less than about 1000 amu, and even less than about 500 amu.

All percentages and ratios used herein, unless otherwise indicated, are by weight.

This application relates, at least in part, to purine-based triazoles, and particularly to hydrophobic, substituted purine-based triazoles that can selectively inhibit certain protein kinases, such as cyclin-dependent kinases (CDKs) (e.g., CDK5), and thereby suppress the cell cycle to promote cytoprotective effects. As discussed in more detail below, certain diseases or disorders are mediated by overactivation of CDKs, which can result in dysregulation of the cell cycle. The hydrophobic, substituted purine-based triazoles of the application can inhibit or suspend the cell cycle machinery and, consequently, may be useful in modulating (e.g., suspending)

cell cycle progression to control cell growth and differentiation. In certain aspects, the hydrophobic, substituted purine-based triazoles can effectively suppress neuronal toxicity induced by amyloid β (Aβ)-oligomers.

In an aspect of the application the hydrophobic, substituted purine-based triazole (or analog thereof) can target, decrease, or inhibit one or more CDKs that play a role in the regulation of the mammalian cell cycle. CDKs that can be inhibited by the application can include CDK1, CDK2, CDK3, CDK4, CDK5, CDK6, CDK7, CDK8 and CDK9. In one example of the application, the hydrophobic, substituted purine-based triazole (or analog thereof) can inhibit CDK5. It will be appreciated that the hydrophobic, substituted purine-based triazole (or analog thereof) can inhibit other protein kinases, such as AHR, GSK3beta, ERK, protein kinase C, her2, raf 1, MEK1, MAP kinase, EGF receptor, PDGF receptor, IGF receptor, PI3 kinase, wee1 kinase, Src, and Abl as well as G proteins and polymerases.

In one embodiment of the application, the hydrophobic, substituted purine-based triazole (or analog thereof) can have the following general formula (I)

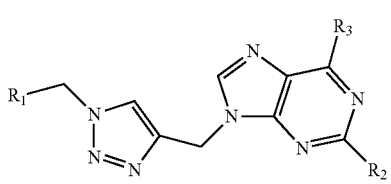

(I)

or a pharmaceutically acceptable salt thereof,
where $R_1$ is a hydrophobic, substituted or unsubstituted, aryl, cyclic, or heterocyclic group; and
where $R_2$ and $R_3$ independently represent substituents selected from the group consisting of hydrogen, halogen, $C_1$-$C_{24}$ alkyl, $C_2$-$C_{24}$ alkenyl, $C_2$-$C_{24}$ alkynyl, $C_3$-$C_{20}$ aryl, $C_6$-$C_{24}$ alkaryl, $C_6$-$C_{24}$ aralkyl, silyl, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, $C_2$-$C_{24}$ alkylcarbonyl (—CO-alkyl), $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO⁻), carbamoyl (—(CO)—NH$_2$), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_1$-$C_{24}$ alkyl)$_2$), mono-substituted arylcarbamoyl (—(CO)—NH-aryl), thiocarbamoyl (—(CS)—NH$_2$), carbamido (—NH—(CO)—NH$_2$), cyano(—CN), isocyano (NC), cyanato (—O—CN), isocyanato (ONC), isothiocyanato (—S—NC), azido (—N=N⁺=N⁻), formyl (—(CO)—H), thioformyl (—(CS)—H), amino (—NH$_2$), mono- and di-($C_1$-$C_{24}$ alkyl)-substituted amino, mono- and di-($C_5$-$C_{20}$ aryl)-substituted amino, $C_2$-$C_{24}$ alkylamido (—NH—(CO)-alkyl), $C_6$-$C_{20}$ arylamido (—NH—(CO)-aryl), imino, alkylimino, arylimino, nitro (—NO$_2$), nitroso (—NO), sulfonic acid (—SO$_2$—OH), sulfonato (—SO$_2$—O⁻), $C_1$-$C_{24}$ alkylsulfanyl (—S-alkyl), arylsulfanyl, $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), phosphono (—P(O)(OH)$_2$), phosphonato (—P(O)(O—)$_2$), phosphinato (—P(O)(O⁻)), phospho (—PO$_2$), and phosphino (—PH$_2$), and where each $R_2$ and $R_3$ being independently unsubstituted or substituted where appropriate by one or more —OH, halogen, amino or alkyl groups.

In some embodiments, $R_1$ can be a fluorinated aryl, cyclic, or heterocyclic group, such as a mono, di, or tri fluorinated phenyl, cyopropane, cylcobutane, cyclohexane, pyrrole, pyridine, pyrimidine, pyrazole, triazole, furan, pyran, indazole, or furazan.

In other embodiments, $R_2$ and $R_3$ can each independently be a hydrogen, a halogen, $C_1$-$C_{24}$ alkyl, $C_2$-$C_{24}$ alkenyl, $C_2$-$C_{24}$ alkynyl, $C_3$-$C_{20}$ aryl, $C_6$-$C_{24}$ alkaryl, $C_6$-$C_{24}$ aralkyl, or an $R_4$—NH—, $R_4$—NH—NH—, NH$_2$—R'—NH— or $R_4$—NH—R'—NH— radical, in which $R_4$ represents a straight- or branched-chain, saturated or unsaturated alkyl radical, an aryl or cycloalkyl radical or a heterocyclic ring and R' represents a straight- or branched-chain, saturated or unsaturated alkylene group or an arylene or cycloalkylene group, $R_4$ and R' each containing 1 to 8 carbon atoms, and where each $R_2$ and $R_3$ can independently be unsubstituted or substituted, where appropriate, by one or more —OH, halogen, amino or alkyl groups.

In some embodiments, the hydrophobic, substituted purine-based triazole or analog thereof can have the following formula (II):

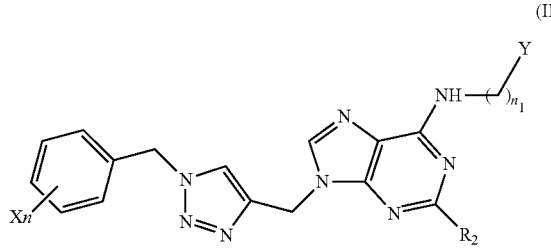

(II)

or a pharmaceutically acceptable salt thereof,
where X is a halogen;
where n is an integer from 0-5;
where $n_1$ is an integer from 1-3;
where Y is substituted or unsubstituted $C_1$-$C_{24}$ alkyl, $C_2$-$C_{24}$ alkenyl, $C_2$-$C_{24}$ alkynyl, $C_3$-$C_{20}$ aryl, $C_6$-$C_{24}$ alkaryl, $C_6$-$C_{24}$ aralky; and $C_1$-$C_4$ fluoroalkyl or $C_1$-$C_4$ perfluoroalkyl.
where $R_2$ is a hydrogen, a halogen, $C_1$-$C_{24}$ alkyl, $C_2$-$C_{24}$ alkenyl, $C_2$-$C_{24}$ alkynyl, $C_3$-$C_{20}$ aryl, $C_6$-$C_{24}$ alkaryl, $C_6$-$C_{24}$ aralkyl, or an $R_4$—NH—, $R_4$—NH—NH—, NH$_2$—R'—NH— or $R_4$—NH—R'—NH— radical, in which $R_4$ represents a straight- or branched-chain, saturated or unsaturated alkyl radical, an aryl or cycloalkyl radical or a heterocyclic ring and R' represents a straight- or branched-chain, saturated or unsaturated alkylene group or an arylene or cycloalkylene group, $R_4$ and R' each containing 1 to 8 carbon atoms, and where $R_2$ is unsubstituted or substituted, where appropriate, by one or more —OH, halogen, amino or alkyl groups. In one example, $R_2$ is hydrogen, Cl, F, an alkyl or substituted alkyl.

In some embodiments, the hydrophobic, substituted purine-based triazole or analog thereof can have the following formula (III):

(III)

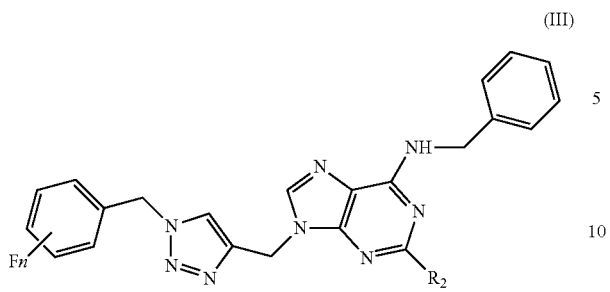

or a pharmaceutically acceptable salt thereof, wherein
where n is an integer from 0-5; and $C_1$-$C_4$ fluoroalkyl or $C_1$-$C_4$ perfluoroalkyl
where $R_2$ is a hydrogen, a halogen, $C_1$-$C_{24}$ alkyl, $C_2$-$C_{24}$ alkenyl, $C_2$-$C_{24}$ alkynyl, $C_3$-$C_{20}$ aryl, $C_6$-$C_{24}$ alkaryl, $C_6$-$C_{24}$ aralkyl, or an $R_4$—NH—, $R_4$—NH—NH—, $NH_2$—R'—NH— or $R_4$—NH—R'—NH— radical, in which R4 represents a straight- or branched-chain, saturated or unsaturated alkyl radical, an aryl or cycloalkyl radical or a heterocyclic ring and R' represents a straight- or branched-chain, saturated or unsaturated alkylene group or an arylene or cycloalkylene group, $R_4$ and R' each containing 1 to 8 carbon atoms, and where $R_2$ is unsubstituted or substituted, where appropriate, by one or more —OH, halogen, amino or alkyl groups. In one example, $R_2$ is hydrogen, Cl, F, an alkyl or substituted alkyl.

In another embodiment of the application, the hydrophobic, substituted purine-based triazole or analog thereof can have the following formula (IV):

(IV)

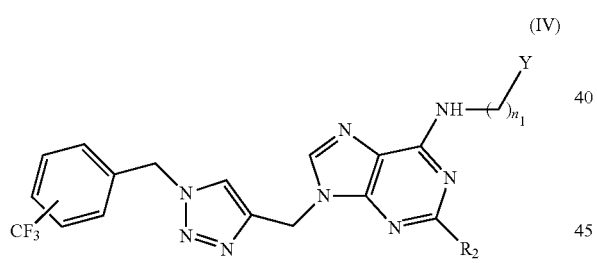

or a pharmaceutically acceptable salt thereof,
where $n_1$ is an integer from 1-3;
where Y is substituted or unsubstituted $C_1$-$C_{24}$ alkyl, $C_2$-$C_{24}$ alkenyl, $C_2$-$C_{24}$ alkynyl, $C_3$-$C_{20}$ aryl, $C_6$-$C_{24}$ alkaryl, $C_6$-$C_{24}$ aralky; and
where $R_2$ is a hydrogen, a halogen, $C_1$-$C_{24}$ alkyl, $C_2$-$C_{24}$ alkenyl, $C_2$-$C_{24}$ alkynyl, $C_3$-$C_{20}$ aryl, $C_6$-$C_{24}$ alkaryl, $C_6$-$C_{24}$ aralkyl, or an $R_4$—NH—, $R_4$—NH—NH—, $NH_2$—R'—NH— or $R_4$—NH—R'—NH— radical, in which R4 represents a straight- or branched-chain, saturated or unsaturated alkyl radical, an aryl or cycloalkyl radical or a heterocyclic ring and R' represents a straight- or branched-chain, saturated or unsaturated alkylene group or an arylene or cycloalkylene group, $R_4$ and R' each containing 1 to 8 carbon atoms, and where $R_2$ is unsubstituted or substituted, where appropriate, by one or more —OH, halogen, amino or alkyl groups. In one example, $R_2$ is hydrogen, Cl, F, an alkyl or substituted alkyl.

In another embodiment of the application, the hydrophobic, substituted purine-based triazole or analog thereof can have the following formula (V):

(V)

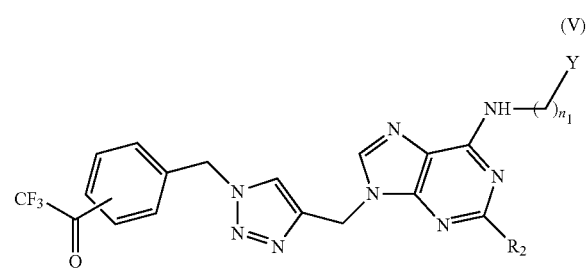

or a pharmaceutically acceptable salt thereof,
where $n_1$ is an integer from 1-3; and $C_1$-$C_4$ fluoroalkyl or $C_1$-$C_4$ perfluoroalkyl.
where Y is substituted or unsubstituted $C_1$-$C_{24}$ alkyl, $C_2$-$C_{24}$ alkenyl, $C_2$-$C_{24}$ alkynyl, $C_3$-$C_{20}$ aryl, $C_6$-$C_{24}$ alkaryl, $C_6$-$C_{24}$ aralky;
where $R_2$ is a hydrogen, a halogen, $C_1$-$C_{24}$ alkyl, $C_2$-$C_{24}$ alkenyl, $C_2$-$C_{24}$ alkynyl, $C_3$-$C_{20}$ aryl, $C_6$-$C_{24}$ alkaryl, $C_6$-$C_{24}$ aralkyl, or an $R_4$—NH—, $R_4$—NH—NH—, $NH_2$—R'—NH— or $R_4$—NH—R'—NH— radical, in which $R_4$ represents a straight- or branched-chain, saturated or unsaturated alkyl radical, an aryl or cycloalkyl radical or a heterocyclic ring and R' represents a straight- or branched-chain, saturated or unsaturated alkylene group or an arylene or cycloalkylene group, $R_4$ and R' each containing 1 to 8 carbon atoms, and where $R_2$ is unsubstituted or substituted, where appropriate, by one or more —OH, halogen, amino or alkyl groups. In one example, $R_2$ is hydrogen, Cl, F, an alkyl or substituted alkyl.

In yet another embodiment of the application, the hydrophobic, substituted purine-based triazole or analog thereof can have the following formula (VI):

(VI)

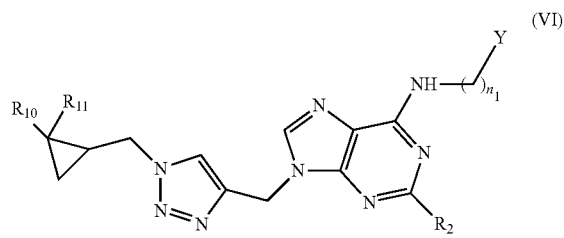

or a pharmaceutically acceptable salt thereof,
where $n_1$ is an integer from 1-3;
where Y is substituted or unsubstituted $C_1$-$C_{24}$ alkyl, $C_2$-$C_{24}$ alkenyl, $C_2$-$C_{24}$ alkynyl, $C_3$-$C_{20}$ aryl, $C_6$-$C_{24}$ alkaryl, $C_6$-$C_{24}$ aralky; and $C_1$-$C_4$ fluoroalkyl or $C_1$-$C_4$ perfluoroalkyl.
where $R_{10}$ and $R_{11}$ are each independently a hydrogen or a halogen; and
where $R_2$ is a halogen atom, $C_1$-$C_{24}$ alkyl, $C_2$-$C_{24}$ alkenyl, $C_2$-$C_{24}$ alkynyl, $C_3$-$C_{20}$ aryl, $C_6$-$C_{24}$ alkaryl, $C_6$-$C_{24}$ aralkyl, or an $R_4$—NH—, $R_4$—NH—NH—, $NH_2$—R'—NH— or $R_4$—NH—R'—NH— radical, in which $R_4$ represents a straight- or branched-chain, saturated or unsaturated alkyl radical, an aryl or cycloalkyl radical or a heterocyclic ring and R' represents a straight- or branched-chain, saturated or unsaturated alkylene group or an arylene or cycloalkylene group, $R_4$ and $R'$ each containing 1 to 8 carbon atoms, and where $R_2$ is unsubstituted or substituted, where appropriate, by one or more —OH, halogen, amino or alkyl groups. In one example, $R_2$ is hydrogen, Cl, F, an alkyl or substituted alkyl.

In another embodiment of the application, the hydrophobic, substituted purine-based triazole or analog thereof can have the following formula (VII):

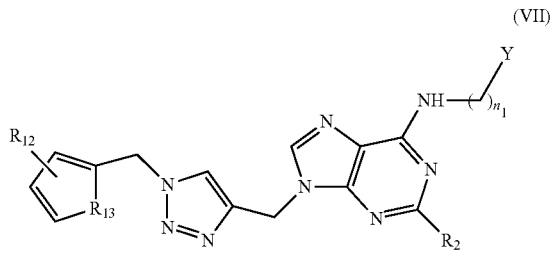

(VII)

or a pharmaceutically acceptable salt thereof,
where $R_{12}$ is hydrogen or a halogen;
where $R_{13}$ is O, N or S;
where $n_1$ is an integer from 1-3;
where Y is substituted or unsubstituted $C_1$-$C_{24}$ alkyl, $C_2$-$C_{24}$ alkenyl, $C_2$-$C_{24}$ alkynyl, $C_3$-$C_{20}$ aryl, $C_6$-$C_{24}$ alkaryl, $C_6$-$C_{24}$ aralky; and $C_1$-$C_4$ fluoroalkyl or $C_1$-$C_4$ perfluoroalkyl.
where $R_2$ is a halogen atom, $C_1$-$C_{24}$ alkyl, $C_2$-$C_{24}$ alkenyl, $C_2$-$C_{24}$ alkynyl, $C_3$-$C_{20}$ aryl, $C_6$-$C_{24}$ alkaryl, $C_6$-$C_{24}$ aralkyl, or an $R_4$—NH—, $R_4$—NH—NH—, $NH_2$—R'—NH— or $R_4$—NH—R'—NH— radical, in which $R_4$ represents a straight- or branched-chain, saturated or unsaturated alkyl radical, an aryl or cycloalkyl radical or a heterocyclic ring and R' represents a straight- or branched-chain, saturated or unsaturated alkylene group or an arylene or cycloalkylene group, $R_4$ and $R'$ each containing 1 to 8 carbon atoms, and where $R_2$ is unsubstituted or substituted, where appropriate, by one or more —OH, halogen, amino or alkyl groups. In one example, $R_2$ is hydrogen, Cl, F, an alkyl or substituted alkyl.

In still other embodiments, the substituted purine-based triazoles can be selected from compounds III-VII, where n is an integer from 0-5; where $R_2$ is a hydrogen, a halogen (e.g., Cl or F), an alkyl or substituted alkyl; where $R_{10}$, $R_{11}$, $R_{12}$ are each independently a hydrogen or a halogen; and where $R_{13}$ is O, N or S.

It will be readily appreciated by those of skill in the art that depending on the substituents, the purine analogs of the present invention can be a racemic mixture or either of a pair of diastereomers or enantiomers.

The hydrophobic, substituted purine-based triazoles (or analogs thereof) can be synthesized using click chemistry. Click chemistry is a convenient way for tethering halogenated and variously substituted aryl moieties to purine-derived alkynes (see, e.g., Spiteri, C. et al., *Angew. Chem. Int. Ed.* 49:31-33, 2010; and Tron, G C et al., *Med. Res. Rev.* 28:278-308, 2008). For instance, click chemistry can be used to couple one or more hydrophobic, halogen-substituted aryl moieties to a purine-derived alkyne through 1,2,3-triazole linkage(s). Introduction of a fluorinated aryl group, for example, can improve the therapeutic efficiency of the substituted purine-based triazoles of the application as a result of the hydrogen bonding interactions with the fluorines at the enzyme active site. Additionally, the halogen-substituted aryl moiety or moieties that form part of the substituted purine-based triazoles impart the substituted purine-based triazoles with sufficient hydrophobicity to facilitate entry of the substituted purine-based triazoles into and across cell membranes.

In one example of the application, a triazole and its fluorinated derivatives can be prepared by a Cu(I)-catalyzed 1,3-dipolar cycloaddition reaction of the corresponding alkyne and azide substrates. As shown below in Scheme 1, synthesis can begin with the reaction of 2,6-dichloropurine (Compound 3) with benzylamine ($^a$) as described, for example, by Oumata, N. et al., *Org. Process Res. Dev.* 13:641-644 (2009). Using the conditions set forth in the Example below, the reaction can be completed in about 15 minutes at about 60° C. 2-chloro-6-benzylaminopurine (Compound 4) can be propargylated using propargyl bromide in DMSO under mild conditions to yield 2-chloro-6-benzylamino-9-(2-propynyl) purine (Compound 5). The Cu(I)-catalyzed azide-alyne click reaction (as described, for example, by Amblard, F. et al., *Chem. Rev.* 109:4207-4220, 2009) of 2-chloro-6-benzylamino-9-(2-propynyl) purine (Compound 5) with fluorinated benzyl azides (which can be prepared in situ from their corresponding benzyl bromides) can then yield 1,4-disubstituted triazoles or, more specifically, 2-chloro-6-benzylamino-9-[1-(2-fluorobenzyl)-1H-1,2,3-triazol-4-yl-methyl] purine (Compound 7), 2-chloro-6-benzylamino-9-[1-(2,6-difluorobenzyl)-1H-1,2,3-triazol-4-yl-methyl]purine (Compound 8), and 2-chloro-6-benzylamino-9-[1-(pentafluorobenzyl)-1H-1,2,3-triazol-4-yl-methyl]purine (Compound 9).

Scheme 1. Synthesis of purine-based fluoroaryl triazoles:

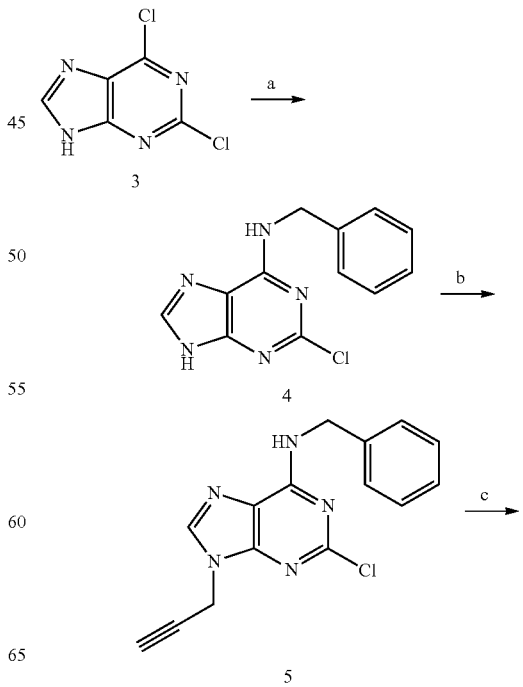

-continued

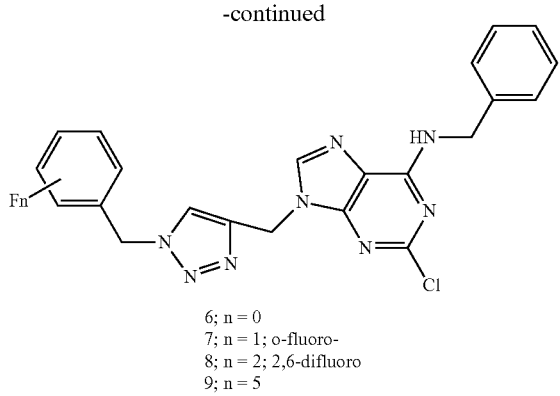

6; n = 0
7; n = 1; o-fluoro-
8; n = 2; 2,6-difluoro
9; n = 5 reagents and conditions: $^a$benzylamine/Et$_3$N/n-BuOH, 60° C./15 min, 95%; $^b$propargyl bromide/K$_2$CO$_3$/DMSO, 0° C./1 h, 80%; $^c$fluorophenylmethyl bromide (or phenylmethyl bromide)/sodium azide/Cu(I)Br/Et$_3$N/DMSO, RT/30 min, 80-89%.

The substituted purine-based triazoles described herein can be incorporated into a variety of formulations for therapeutic administration. More particularly, the substituted purine-based triazoles can be formulated into pharmaceutical compositions by combination with appropriate, pharmaceutically acceptable carriers or diluents, and may be formulated into preparations in solid, semi-solid, liquid or gaseous forms, such as tablets, capsules, pills, powders, granules, dragees, gels, slurries, ointments, solutions, suppositories, injections, inhalants and aerosols. As such, administration of the substituted purine-based triazoles can be achieved in various ways, including oral, buccal, rectal, parenteral, intraperitoneal, intradermal, transdermal, intracheal, etc., administration. Moreover, the substituted purine-based triazoles can be administered in a local rather than systemic manner, for example via injection of the compound directly into a tissue being treated, often in a depot or sustained release formulation.

In addition, the substituted purine-based triazoles can be administered in a targeted drug delivery system, for example, in a liposome coated with tissue or cell-specific antibody. Such liposomes will be targeted to and taken up selectively by the tissue or cell.

Formulations for use in the application are found in Remington's Phannaceutical Sciences (Mack Publishing Company, Philadelphia, Pa., 17th ed. (1985)), which is incorporated herein by reference. Moreover, for a brief review of methods for drug delivery, see, Langer, Science 249:1527-1533 (1990), which is incorporated herein by reference. The pharmaceutical compositions described herein can be manufactured in a manner that is known to those of skill in the art, i.e., by means of conventional mixing, dissolving, granulating, dragee-making, levigating, emulsifying, encapsulating, entrapping or lyophilizing processes. The following methods and excipients are merely exemplary and are in no way limiting.

For injection, the substituted purine-based triazoles can be formulated into preparations by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. The substituted purine-based triazoles may be formulated in aqueous solutions, such as in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the substituted purine-based triazoles can be formulated by combining with pharmaceutically acceptable carriers that are well known in the art. Such carriers enable the compounds to be formulated as tablets, pills, dragees, capsules, emulsions, lipophilic and hydrophilic suspensions, liquids, gels, syrups, slurries, suspensions and the like, for oral ingestion by a patient to be treated. Pharmaceutical preparations for oral use can be obtained by mixing the compounds with a solid excipient, optionally grinding a resulting mixture, and processing the mixture of grammes, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores can be provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds described herein are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas, or from propellant-free, dry-powder inhalers. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base, such as lactose or starch.

The substituted purine-based triazoles may be formulated for parenteral administration by injection, e.g., by bolus injection or continuous infusion. Formulations for injection may be presented in unit dosage form, e.g., in ampules or in multidose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain stabilizers or agents, which increase the solubility of the compounds to allow for the preparation of highly concentrated solutions. Alternatively, the substituted purine-based triazoles may be in powder form for constitution with a suitable vehicle, e.g., sterile pyrogen-free water, before use.

The substituted purine-based triazoles may also be formulated in rectal compositions such as suppositories or retention enemas, e.g., containing conventional suppository bases such as cocoa butter, carbowaxes, polyethylene glycols or other glycerides, all of which melt at body temperature, yet are solidified at room temperature.

In addition to the formulations described previously, the substituted purine-based triazoles may also be formulated as a depot preparation. Such long acting formulations may be administered by implantation (for example subcutaneously or intramuscularly) or by intramuscular injection. Thus, for example, the substituted purine-based triazoles may be formulated with suitable polymeric or hydrophobic materials (for example as an emulsion in an acceptable oil) or ion exchange resins, or as sparingly soluble derivatives, for example, as a sparingly soluble salt.

Alternatively, other delivery systems for hydrophobic substituted purine-based triazoles may be employed. Liposomes and emulsions are well known examples of delivery vehicles or carriers for hydrophobic drugs. Certain organic solvents such as dimethylsulfoxide also may be employed, although usually at the cost of greater toxicity.

Additionally, the substituted purine-based triazoles may be delivered using a sustained-release system, such as semipermeable matrices of solid hydrophobic polymers containing the therapeutic agent. Various types of sustained-release materials have been established and are well known by those skilled in the art. Sustained-release capsules may, depending on their chemical nature, release the compounds for a few weeks up to over 100 days.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Pharmaceutical compositions can also include compositions wherein the substituted purine-based triazoles are contained in a therapeutically effective amount. The amount of composition administered will, of course, be dependent on the subject being treated, on the subject's weight, the severity of the affliction, the manner of administration and the judgment of the prescribing physician. Determination of an effective amount is well within the capability of those skilled in the art, especially in light of the detailed disclosure provided herein.

For any compound used in a method described herein, a therapeutically effective dose can be estimated initially from cell culture assays. For example, a dose can be formulated in animal models to achieve a circulating concentration range that includes the $IC_{50}$ as determined in cell culture (i.e., the concentration of test compound that is lethal to 50% of a cell culture), or the $IC_{100}$ as determined in cell culture (i.e., the concentration of compound that is lethal to 100% of a cell culture). Such information can be used to more accurately determine useful doses in humans. Initial dosages can also be estimated from in vitro or in vivo data.

Initial dosages can also be formulated by comparing the effectiveness of the compounds described herein in cell culture assays with the effectiveness of known drugs. For instance, initial dosages can be formulated by comparing the effectiveness of the substituted purine-based triazoles described herein in cell culture assays with the effectiveness of a CDK inhibitor, such as Roscovitine. In this method, an initial dosage can be obtained by multiplying the ratio of effective concentrations obtained in cell culture assay for the substituted purine-based triazoles described herein and a known CDK inhibitor by the effective dosage of the known CDK inhibitor. For example, if a substituted purine-based triazole described herein is twice as effective in cell culture assay than Roscovitine, an initial effective dosage of the substituted purine-based triazoles would be one-half the known dosage for Roscovitine. Using these initial guidelines one having ordinary skill in the art could determine an effective dosage in humans.

Moreover, toxicity and therapeutic efficacy of the compounds described herein can be determined by standard pharmaceutical procedures in cell cultures or experimental animals, e.g., by determining the $LD_{50}$, (the dose lethal to 50% of the population) and the $ED_{50}$ (the dose therapeutically effective in 50% of the population). The dose ratio between toxic and therapeutic effect is the therapeutic index and can be expressed as the ratio between $LD_{50}$ and $ED_{50}$. Substituted purine-based triazoles, which exhibit high therapeutic indices are preferred. The data obtained from these cell culture assays and animal studies can be used in formulating a dosage range that is not toxic for use in human. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. (See, e.g., Fingl et al., 1975, In: The Pharmacological Basis of Therapeutics, Ch. 1, p. 1).

Dosage amount and interval may be adjusted individually to provide plasma levels of the active compound, which are sufficient to maintain therapeutic effect. Usual patient dosages for oral administration range from about 50-2000 mg/kg/day, commonly from about 100-1000 mg/kg/day, preferably from about 150-700 mg/kg/day and most preferably from about 250-500 mg/kg/day. Preferably, therapeutically effective serum levels will be achieved by administering multiple doses each day. In cases of local administration or selective uptake, the effective local concentration of the drug may not be related to plasma concentration. One having skill in the art will be able to optimize therapeutically effective local dosages without undue experimentation.

The substituted purine-based triazoles described herein can be used either in vitro or in vivo for a variety of purposes. As discussed previously, in some embodiments of the application, the substituted purine-based triazoles can be used to inhibit protein kinases, G proteins and polymerases. Protein kinases which can be inhibited using the purine-based triazoles described herein include, but are not limited to, cyclin-dependent kinases (CDKs), MAP kinases (p38, ERK), (MAPK/MEK/MEKK), cAMP-dependent kinase, c-GMP-dependent kinase, Calmodulin-dependent kinase, CSK (C-src like kinase) pp 60 c-src, myosin light chain kinase, JNK kinase, IKB kinase, Protein kinase C, etc. In a presently preferred embodiment, the protein kinase is a CDK. Such CDKs include CDK1 (or, interchangeably, CDC2) and CDK2-CDK8. G proteins that can be inhibited using the substituted purine-based triazoles include, but are not limited to, GTP binding proteins. Polymerases, which can be inhibited using the purine analogs of the present invention include, but are not limited to, DNA polymerase a, DNA polymerase 6, DNA topoisomerase I, topoisomerase II, phosphatases, telomerases, etc. Other protein kinases, G proteins and polymerases which can be inhibited using the substituted purine-based triazoles described herein will be known to those of skill in the art.

In other embodiments, the substituted purine-based triazoles can be used in a method for inhibiting at least one CDK in a subject. Due to the key role of CDKs in regulating the cell cycle and cellular proliferation, the substituted purine-based triazoles (or analogs thereof) disclosed herein may act as reversible cytostatic agents, which may be useful in the treatment of any disease process featuring abnormal cell cycle or cellular proliferation, including, but not limited to, abnormal stimulation of endothelial cells (e.g., atherosclerosis), neoplastic disorders, solid tumors and tumor metastasis, benign tumors, for example, hemangiomas, acoustic neuromas, neurofibromas, trachomas, and pyogenic granulomas, cancer, vascular malfunctions, abnormal wound healing, inflammatory and immune disorders, Bechet's disease, gout or gouty arthritis, abnormal angiogenesis accompanying, for example, rheumatoid arthritis, psoriasis, alopecia, diabetic retinopathy, other ocular angiogenic diseases, such as retinopathy of prematurity (retrolental fibroplastic), macular degeneration, corneal graft rejection, neuroscular glaucoma and Oster Webber syndrome, fungal, parasitic and viral infections, such as cytomegaloviral infections, neurological disorders, stroke, neurofibromatosis, endotoxic shock, hypertrophic scar formation, inflammatory bowel disease, transplant rejection, vascular smooth muscle cell proliferation associated with atherosclerosis, pulmonary fibrosis, arthritis, glomerulonephritis, restenosis following angioplasty or vascular surgery, and other post-surgical stenosis and restenosis.

In one specific embodiment, the substituted purine-based triazoles can be administered to a subject to treat a proliferative disorder of the subject. The proliferative disorder described herein can include, for example cardiovascular disorders, such as restenosis and cardiomyopathy, neoplastic disorders, auto-immune disorders, such as glomerulonephritis and rheumatoid arthritis, dermatological disorders such as psoriasis, anti-inflammatory, anti-fungal, antiparasitic disorders, such as malaria, emphysema and alopecia. In these disorders, the substituted purine-based triazoles described herein may induce apoptosis or maintain stasis within the desired cells as required.

The substituted purine-based triazoles described herein can inhibit any of the steps or stages in the cell cycle, for example, formation of the nuclear envelope, exit from the quiescent phase of the cell cycle (G0), G1 progression, chromosome decondensation, nuclear envelope breakdown, START, initiation of DNA replication, progression of DNA replication, termination of DNA replication, centrosome duplication, G2 progression, activation of mitotic or meiotic functions, chromosome condensation, centrosome separation, microtubule nucleation, spindle formation and function, interactions with microtubule motor proteins, chromatid separation and segregation, inactivation of mitotic functions, formation of contractile ring, and cytokinesis functions. In particular, the substituted purine-based triazoles may influence certain gene functions such as chromatin binding, formation of replication complexes, replication licensing, phosphorylation or other secondary modification activity, proteolytic degradation, microtubule binding, actin binding, septin binding, microtubule organising centre nucleation activity and binding to components of cell cycle signalling pathways.

In one embodiment, the proliferative disorder can be a neoplastic disorder. By way of example, neoplastic disorders treatable by the compounds described herein can include, but are not limited to: carcinoma, including that of the bladder, breast, colon, kidney, liver, lung, including small cell lung cancer, esophagus, gall bladder, ovary, pancreas, stomach, cervix, thyroid, prostate, and skin, including squamous cell carcinoma; hematopoietic tumors of lymphoid lineage, including leukemia, acute lymphocytic leukemia, acute lymphoblastic leukemia, B-cell lymphoma, T-cell lymphoma, Hodgkin's lymphoma, non-Hodgkin's lymphoma, hairy cell lymphoma, and Burkett's lymphoma; hematopoietic tumors of myeloid lineage, including acute and chronic myelogenous leukemias, myelodysplastic syndrome, and promyelocytic leukemia; tumors of mesenchymal origin, including fibrosarcoma and rhabdomyosarcoma; tumors of the central and peripheral nervous system, including astrocytoma, neuroblastoma, glioma, and schwannomas; and other tumors, including melanoma, seminoma, teratocarcinoma, osteosarcoma, xenoderoma pigmentosum, keratoctanthoma, thyroid follicular cancer, and Kaposi's sarcoma.

Neoplastic disorders, such as cancer are typically characterized by abnormal cell division as a result of dysfunctional signaling cascades and/or checkpoint control within the cell cycle. For example, the first stage of the cell cycle, which is mediated by a highly controlled kinase family, consists of a cascade of protein phosphorylations that relay a cell from one stage to the next. The second stage is a set of checkpoints that monitor completion of critical events and delay progression to the next stage, if necessary. CDKs are critically important in the first stage, and their overactivity can result in disruption of the cell cycle and progression to uncontrolled cell growth. By inhibiting at least one CDK in the subject, the cell cycle in neoplastic or potentially neoplastic cells can be maintained or suspended so that the cells do not become hyperproliferative.

In another embodiment, the substituted purine-based triazoles can be administered to a subject to treat a neurological or neurodegenerative disorder including central nervous system disorders or peripheral nervous system disorders. Examples of neurological disorders treated by the compounds and compositions described herein can include, but are not limited to, Alzheimer's disease, Parkinson's disease, Huntington's disease, amyotrophic lateral sclerosis, multiple sclerosis, elderly dementia, Tay-Sach's disease, Sandhoffs disease, Hurler's syndrome, Krabbe's disease, central or peripheral nervous system injury, epilepsy, multiple sclerosis, central or peripheral nervous system trauma, stroke, Asperger syndrome, Autism, Attention deficit hyperactivity disorder (ADHD), Cerebral palsy, Dyslexia, seizures, Mild Cognitive Impairment (MCI), retinitis pigmentosa, spinal muscular atrophy, motor neuron disease, bipolar disorder, cerebellar degeneration or age associated memory impairment.

In one example, the substituted purine-based triazoles described herein can be used to treat a subject suffering from a neurological disorder mediated by Aβ, such as Alzheimer's disease. The substituted purine-based triazoles can be can administered at a therapeutically effective amount in a pharmaceutical composition that includes the purine-based triazole and a pharmaceutical carrier. The therapeutically effective amount of the pharmaceutical composition can be administered to the subject via an appropriate route. Upon administration to the subject, the substituted purine-based triazole can readily traverse neuronal cell membranes as a result of the compound's hydrophobic nature. The substituted purine-based triazole can then selectively inhibit CDK5 due to the hydrogen bonding interactions at the enzyme's active site Inhibition of CDK5 can consequently prevent or mitigate tau-hyperphosphorylation, increase levels of synaptic markers, and suppress or suspend the neuronal cell cycle to promote neuronal survival.

In another embodiment, the substituted purine-based triazoles can be used as an antiviral agent. For example, the substituted purine-based triazoles described herein can be used in the preparation of a medicament for treating a viral disorder, such as human cytomegalovirus (HCMV), herpes simplex virus type 1 (HSV-1), human immunodeficiency virus type 1 (HIV-1), and varicella zoster virus (VZV).

In a more preferred embodiment, the substituted purine-based triazoles can be administered at an amount effective to inhibit one or more of the host cell CDKs involved in viral replication (Wang D, De la Fuente C, Deng L, Wang L, Zilberman I, Eadie C, Healey M, Stein D, Denny T, Harrison L E, Meijer L, Kashanchi F Inhibition of human immunodeficiency virus type 1 transcription by chemical cyclin-dependent kinase inhibitors. J. Virol. 2001; 75: 7266-7279). As defined herein, an anti-viral effect within the scope of the present invention may be demonstrated by the ability to inhibit at least one CDK.

In a particular embodiment, the substituted purine-based triazoles can be used in the treatment of a viral disorder which is CDK dependent or sensitive. CDK dependent disorders are associated with an above normal level of activity of one or more CDK enzymes. Such disorders can be associated with an abnormal level of activity of CDK. A CDK sensitive disorder is a disorder in which an aberration in the CDK level is not the primary cause, but is downstream of the primary metabolic aberration. In such scenarios, CDK can be said to be part of the sensitive metabolic pathway and CDK inhibitors may therefore be active in treating such disorders.

Another aspect of the invention relates to the use of the substituted purine-based triazoles, or pharmaceutically acceptable salts thereof, in the preparation of a medicament for treating diabetes. In a particular embodiment, the diabetes is type II diabetes.

GSK3 is one of several protein kinases that phosphorylate glycogen synthase (GS). The stimulation of glycogen synthesis by insulin in skeletal muscle results from the dephosphorylation and activation of GS. GSK3's action on GS thus results in the latter's deactivation and thus suppression of the conversion of glucose into glycogen in muscles.

Type II diabetes (non-insulin dependent diabetes mellitus) is a multi-factorial disease. Hyperglycaemia is due to insulin resistance in the liver, muscles, and other tissues, coupled with impaired secretion of insulin. Skeletal muscle is the main site for insulin-stimulated glucose uptake, there it is either removed from circulation or converted to glycogen. Muscle glycogen deposition is the main determinant in glucose homeostasis and type II diabetics have defective muscle glycogen storage. There is evidence that an increase in GSK3 activity is important in type II diabetes [Chen, Y. H.; Hansen, L.; Chen, M. X.; Bjorbaek, C.; Vestergaard, H.; Hansen, T.; Cohen, P. T.; Pedersen, 0. Diabetes, 1994, 43, 1234]. Furthermore, it has been demonstrated that GSK3 is over-expressed in muscle cells of type II diabetics and that an inverse correlation exists between skeletal muscle GSK3 activity and insulin action [Nikoulina, S. E.; Ciaraldi, T. P.; Mudaliar, S.; Mohideen, P.; Carter, L.; Henry, R. R. Diabetes, 2000, 49, 263]. GSK3 inhibition using the substituted purine based triazoles described herein is therefore of therapeutic significance in the treatment of diabetes, particularly type II, and diabetic neuropathy.

Yet another embodiment of the application relates to the use of the substituted purine-based triazoles in the preparation of a medicament for treating alopecia. Hair growth is controlled by the Wnt signalling pathway, in particular Wnt-3. In tissue-culture model systems of the skin, the expression of non-degradable mutants of β-catenin leads to a dramatic increase in the population of putative stem cells, which have greater proliferative potential [Zhu, A. J.; Watt, F. M. Development, 1999, 126, 2285]. This population of stem cells expresses a higher level of non-cadherin-associated .beta.-catenin [DasGupta, R.; Fuchs, E. Development, 1999, 126, 4557], which may contribute to their high proliferative potential. Moreover, transgenic mice overexpressing a truncated .beta.-catenin in the skin undergo de novo hair-follicle morphogenesis, which normally is only established during embryogenesis. The ectopic application of GSK3 inhibitors may therefore be therapeutically useful in the treatment of baldness and in restoring hair growth following chemotherapy-induced alopecia. A further aspect of the application therefore relates to a method of treating a GSK3-dependent disorder, said method comprising administering to a subject in need thereof, substituted purine-based triazole, or a pharmaceutically acceptable salt thereof, as defined above in an amount sufficient to inhibit GSK3.

The following example is for the purpose of illustration only and is not intended to limit the scope of the claims, which are appended hereto.

EXAMPLE

In this example, we synthesized a series of fluorinated purine-based triazoles and assayed their protective effect against Aβ-induced neurotoxicity in hippocampal slice cultures. We reasoned that a fluoroaryl group distant from the nucleoside moiety, through optimal hydrophobic interactions at the enzyme active site, could impart selective CDK5 inhibitory effect, effectively causing neuronal cell cycle suppression.

Selective inhibition of CDK5/p25 over CD5/p35 and other CDK kinases is a desired goal for the treatment of a number of CDK dependent disorders, including neurological disorders, such as Alzheimer's disease and proliferative disorders, such as cancer. Roscovitine is currently undergoing clinical trials as kinase inhibitor in AD, although it is not a selective inhibitor of CDK5. Similarly, a flavone-derived compound, Flavopiridol has also been shown to be effective as a broad-spectrum CDK inhibitor. Perhaps due to this nonspecificity to selective CDKs, it is more cytotoxic and has other harmful effects. It is therefore desirable to design selective CDK inhibitors that show neuroprotective effects, without attendant harmful side effects. We anticipated that modulating the hydrophobicity effect of the compounds by attaching the fluoroaryl rings to the Roscovitine analogues through 1,2,3-triazole linkage might make these compounds selective inhibitors of CDKs. We adopted Sharpless-Huisgen's Click chemistry as a convenient technique for tethering fluorinated and variously substituted aryl moieties to purine derived alkynes, and investigated the neuroprotective effects of these fluoroaryl substituted purine based 1,2,3-triazoles along with those of Flavopiridol (1) and Roscovitine (2) for AD and related neurological diseases.

In this Example, we used a convenient assay for neuronal cell death, which was induced by incubation with Aβ oligomers in hippocampal slice cultures. The binding of propidium iodide (PI) with DNA of dead cells gives characteristic fluorescence that could be followed by fluorescence microscopy. Since PI is impermeable to live cell membranes, the observed fluorescence is indicative of the extent of dead cell populations. Using this technique, we have found that incubation of hippocampal neuronal cells with Aβ results in significant neuronal cell death after a duration of 48 h (FIG. 1).

Materials and Methods

Benzylamine (>99.5%), 1-butanol (anhydrous, 99.8%), benzyl bromide (reagent grade, 98%) triethylamine (>99.5%), dimethyl sufoxide (ACS reagent, >99.9%), potassium carbonate (ACS reagent, >99.9%), Copper(I)bromide (98%), 2-flurobenzyl bromide (98%), 2,6-difluorobenzylbromide (97%), pentafluorobenzylbromide (99%), and 2,6-dichloropurine (97%) were obtained from Aldrich and used as received.

$^1$H NMR spectra (400 MHz), $^{13}$C NMR spectra (100 MHz), and $^{19}$F NMR spectra (376 MHz) were obtained on a Varian Inova 400 MHz spectrometer in DMSO-$d_6$ solutions. $^{19}$F NMR spectra were referenced to $CFC_3$ ($\delta^{19}F=0$), and $^1$H, and $^{13}$C NMR were referenced to the residual solvent signals or internal tetramethylsilane. EI/MS was obtained using solid probe on a Hewlett Packard HPs 5890 GC/MS instrument.

Computational Methodology

The CDK5 protein structure was obtained from its Roscovitine co-crystal PDB entry, "1UNL", and minimized using Dreiding force-field. This protein structure was used to first identify potential ligand binding regions as follows: The entire protein was scanned for potential binding regions with no assumption on the binding site. The entire molecular surface of the predicted structure is mapped and spheres representing the empty volume of the protein are generated (using the Sphgen program in DOCK4.0 suite of programs). The entire set of protein spheres is partitioned into ~30 to 50 overlapping cubes of 10 to 14 Å sides. The 1000 poses are generated for each of these 30-50 regions and the results compared to select the most promising two or three putative binding regions. This bind site scanning procedure is used for agonists and antagonists separately with the hypothesis that an agonist might prefer a site different than an antagonist.

The putative binding regions identified in the above scanning procedure were docked with Roscovitine, and compounds 7 and 9 separately, using Goddard's DarwinDock/GenDock methodology 20 to predict the binding region and pose preferred by these molecules. The top scoring binding poses were compared in terms of their pharmacophore and their relative binding energies.

Preparation of Aβ Oligomers 1.0 mg of Aβ1-42 peptide was dissolved in 120 μL of hexafluoroisopropanol for 60 min at room temperature, and placed back on ice for 5-10 min. Hexafluoroisopropanol was evaporated overnight in the hood at room temperature. The sample was dissolved by 100% DMSO by adding 20 μL of fresh anhydrous DMSO (Sigma Hybri-Max) to 0.45 mg of the peptide, and diluted to 5 mM peptide stock into medium. Diluted peptide was incubated at 4° C. for 24 h, and then centrifuged at 14,000 g for 10 min in the cold. Before treating slice culture with Aβ oligomers, the oligomers were incubated at room temperature for 20 h.

Preparation of Hippocampal Slice Cultures

Hippocampal slice cultures were prepared from 7-10 day-old mouse pups. Slices were cut at 400 μm on a McIlwain tissue chopper, transferred to Millicell (Millipore Corp., Bedford, Mass.) membrane inserts (0.4 μm), and placed in 6-well culture plated. The upper surfaces of the slices were exposed to a humidified 37° C. atmosphere containing 5% $CO_2$. Slice culture media consisted of basal Eagles medium with Earle's balanced salt solution, 20% heat-inactivated horse serum, enriched with glucose to a concentration of 5.6 mM. The medium was changed every other day. Slices were examined periodically for viability, and any dark or abnormal slices were discarded.

Experimental Treatment of Aβ Oligomers to Organotypic Hippocampal Slice Culture

The effects of Aβ oligomers were tested in the slices which had been maintained for 15-20 days in vitro. All reagents were added to serum free medium (no horse serum). Aβ oligomers were added to cultures in serum free medium. Vehicles were treated the same way except with no peptide. The slices were pretreated with compounds 6, 7, 8, 9 or cell cycle inhibitor Flavopiridol or Roscovitine (1 μM) for 1 h before Aβ oligomers treatment.

Assessment of Neuronal Cell Death by PI Staining

To analyze the degree of hippocampal neuronal cell death, hippocampal slices were stained by adding PI into slice culture medium at a concentration of 5 μg/mL. At indicated times after Aβ oligomers treatment, the degree of hippocampal neuronal death was evaluated by microscopic observation of PI uptake as described previously. 23 Images were acquired through an AxioCam camera on an Axiovert 200M microscope (Zeiss, Thornwood, N.Y.). The intensity of the fluorescence was quantitatively analyzed using Scion Image. The images were expressed as an arbitrary unit of PI uptake.

Statistical Analysis

Data were expressed as the means±S.E. of the values from the number of experiments indicated in the corresponding figures. Differences between groups were examined for statistical significance using one-way analysis of variance with an unpaired Students t-test. A p value less than 0.05 is denoted to have statistical significance.

Synthesis of Compounds

2-Chloro-6-benzylaminopurine (4)

To a suspension of 2,6-dichloropurine (110 mg, 0.52 mmol) in n-butanol (3 mL), benzylamine (57 mg, 0.52 mmol) and triethylamine (72 mg, 0.79 mmol) was added. The mixture was stirred and heated at 60° C. for 15 min. The resulting precipitate was filtered, washed with water (20 mL) and methanol (10 mL), and air-dried overnight. Compound 4 (130 mg, 95%) was obtained as an off-white solid: mp 262° C.; EI/MS (m/z (relative %)): 259 (19, M$^{+\cdot}$), 260 (14), 261 (17%), 106 (100), 91 (77); $^1$H NMR (400 MHz, DMSO) δ 8.15 (s, 1H), 7.25-7.34 (m, 5H), 4.66 (d, J=6 Hz, 2H); $^{13}$C NMR (100 MHz, DMSO) δ 155.0 (s) 153.1 (s), 150.7 (s), 140.2 (d, $^1J_{C-H}$=200 Hz), 139.6 (s), 128.5 (d, $^1J_{C-H}$=158 Hz, 127.5 (d, $^1J_{C-H}$=157 Hz), 127.0 (d, $^1J_{C-H}$=158 Hz) 118.1 (s), 43.4 (t, $^1J_{C-H}$=139 Hz).

2-Chloro-6-benzylamino-9-(2-propynyl)purine (5)

A solution of 2-chloro-6-benzylaminopurine (1.1 g, 3.8 mmol), in DMSO (5 mL) was cooled to 0° C., potassium carbonate (0.79 g, 5.7 mmol) and propargyl bromide (0.45 g, 3.8 mmol) was added to the contents, and stirred for 1 h at 0° C. Water (20 mL) was then added to the reaction mixture, and the resulting yellow precipitate was filtered and washed with excess water (50 mL). Compound 5 (1.1 g, 80%) was obtained as an off-white solid upon successive recrystallization from dichloromethane and ethyl acetate: mp 180° C.; EI/MS (m/z (relative %)): 297 (63, M$^{+\cdot}$), 298 (15), 299 (23), 258 (46), 91(100); $^1$H NMR (400 MHz, DMSO) δ 8.23 (s, 1H), 7.21-7.38 (m, 5H), 5.03 (bs, 2H), 4.62 (d, J=6 Hz, 2H), 3.51 (s, 1H). $^{13}$C NMR (100 MHz, DMSO) δ 155.6 (s), 154.0 (s), 150.3 (s), 140.7 (d, $^1J_{C-H}$=214 Hz) 139.9 (s), 128.9 (d, $^1J_{C-H}$=159 Hz), 127.9 (d, $^1J_{C-H}$=157 Hz), 126.8 (d, $^1J_{C-H}$=158 Hz), 118.1 (s), 78.5 (t, $^2J_{C-H}$=9 Hz) 76.7 (dt, $^1J_{C-H}$=252 Hz, $^3J_{C-H}$=4 Hz), 43.8 (t, $^1J_{C-H}$=126 Hz), 33.3 (t, $^1J_{C-H}$=139 Hz).

Procedure A: Synthesis of 2-Chloro-6-benzylamino-9-(1-benzyl-1H-1,2,3-triazol-4-yl-methyl)purine (6)

Benzyl bromide (110 mg, 0.58 mmol) was added dropwise to a solution of sodium azide (42 mg, 0.64 mmol) in DMSO (5 mL, and stirred at room temperature for 15 min. Compound 5 (173 mg, 0.58 mmol), triethylamine (6 mg, 0.06 mmol) and CuBr (8 mg, 0.6 mmol) were added to the contents in that order, and the reaction mixture was stirred at room temperature for 30 min. The reaction mixture was poured into ice-cold water (20 mL), and the resulting off-white precipitate was filtered and washed with dilute NH$_4$OH (20 mL) and water (50 mL) to give the compound 6 (200 mg 80%) essentially pure by NMR; mp 235° C. EI/MS (m/z (relative %)): 430 (32, M$^+$), 431 (11), 432 (13), 258 (54), (100); $^1$H NMR (400 MHz, DMSO) δ 8.23 (s, 1H), 8.15 (s, 1H), 7.40-7.17 (m, 10H), 5.56 (s, 2H), 5.40 (s, 2H), 4.62 (d, J=6 Hz, 2H); $^{13}$C NMR (100 MHz, DMSO) δ 155.6 (s), 153.9 (s), 150.3 (s), 143.1 (d, $^1J_{C-H}$=199 Hz), 141.9 (s), 139.9 (s), 136.51 (s), 129.4 (d, $^1J_{C-H}$=160 Hz), 128.9 (d, $^1J_{C-H}$=159 Hz), 128.8 (d, $^1J_{C-H}$=159 Hz), 128.5 (d, $^1J_{C-H}$=158 Hz), 127.9 (overlapping doublets), 127.4 (overlapping doublets), 124.4 (d, $^1J_{C-H}$=200 Hz) 118.6 (s), 53.4 (t, $^1J_{C-H}$=145 Hz), 43.7 ((t, $^1J_{C-H}$=135 Hz), 38.9 (t, $^1J_{C-H}$=139 Hz).

2-Chloro-6-benzylamino-9-[1-(2-fluorobenzyl)-1H-1,2,3-triazol-4-yl-methyl]purine (7)

Compound 7 was obtained as an off white solid (85%), using procedure A: mp 240° C.; EI/MS (m/z (relative %)): 448 (44, M$^+$), 449 (14), 450 (17), 258 (83), 109 (100), 91 (67); $^1$H NMR (400 MHz, DMSO) δ 8.23 (s, 1H), 8.17 (s, 1H), 7.43-7.10 (m, 9H), 5.60 (s, 2H), 5.38 (s, 2H), 4.60 (d, J=6 Hz, 2H); $^{19}$F NMR (376 MHz, CDCl$_3$) −117.37 (dd, J=14 Hz, 8 Hz); $^{13}$C NMR (100 MHz, DMSO) δ 160.7 (d, $^1J_{C-H}$=248 Hz), 155.6 (s), 153.8 (s), 150.3 (s), 143.1 (d, $^1J_{C-H}$=199 Hz), 142.0 (s), 139.9 (s), 132.4 (d, $^1J_{C-H}$=165 Hz) 131.3 (dd, $^1J_{C-H}$=160 Hz, $^3J_{CF}$=4 Hz), 128.9 (d, $^1J_{C-H}$=156 Hz) 127.9 (d, $^1J_{C-H}$=150 Hz), 127.4 (d, $^1J_{C-H}$=160 Hz), 125.5 (d, $^1J_{C-H}$=150 Hz), 124.5 (d, $^1J_{C-H}$=200 Hz), 123.3 (d, $^2J_{C-F}$=26 Hz), 118.6 (s), 116.2 (dd, J$_{CH}$=170 Hz, $^2J_{C-H}$=21 Hz) 47.6 (t, $^1J_{C-H}$=130), 43.8 (t, =133 Hz), 38.9 (t, $^1J_{C-H}$=143 Hz).

2-Chloro-6-benzylamino-9-[1-(2,6-difluorobenzyl)-1H-1,2,3-triazol-4-yl-methyl]purine (8)

Compound 8 was obtained as an off white solid (84%), using the procedure A: mp 239° C.; EI/MS (m/z (relative %)): 466 (52, M$^+$), 467 (19), 468 (22), 258 (77), 127 (100), 91 (73); $^1$H NMR (400 MHz, DMSO) δ 8.20 (s), 8.16 (s), 7.05-7.47 (m, 8H), 5.60 (s, 2H), 5.37 (s, 2H), 4.61 (d, J$_{H-H}$=5.5 Hz, 2H). $^{19}$F NMR (376 MHz, CDCl$_3$) δ −114.10; $^{13}$C NMR (100 MHz, DMSO) δ 161.4 (dd, $^1J_{C-F}$=248 Hz, $^2J_{C-H}$=7 Hz), 155.5 (s), 153.8 (s), 150.3 (s), 143.01 (s), 142.03 (d, $^1J_{C-H}$=199 Hz), 139.9 (s), 132.4 (dt, $^1J_{C-H}$=166 Hz), $^3J_{C-F}$=10 Hz), 128.9 (dd, $^1J_{C-H}$=159 Hz, $^2J_{C-H}$=6 Hz), 127.9 (dm, $^1J_{C-H}$=154 Hz), 127.5 (d, $^1J_{C-H}$=164 Hz), 124.6 (d, $^1J_{C-H}$=197 Hz), 118.6 (s), 112.6 (ddd, $^1J_{C-H}$=166 Hz, $^2J_{C-F}$=19 Hz, $^2J_{C-H}$=6 Hz), 111.8 (t, $^2J_{C-F}$=19 Hz) 43.7 (t, $^1J_{C-H}$=150 Hz), 41.4 (t, $^1J_{C-H}$=150 Hz), 38.6 (t, $^1J_{C-H}$=150 Hz).

2-Chloro-6-benzylamino-9-[1-(pentafluorobenzyl)-1H-1,2,3-triazol-4-yl-methyl]purine (9)

Compound 9 was obtained as an off white solid (89%), using the procedure A: mp 225° C.; EI/MS (m/z (relative %)): 520 (24%, M$^+$), 521 (6), 522 (9%), 258 (73), 181 (69), 106 (64), 91 (100); $^1$H NMR (400 MHz, DMSO) δ 8.22 (s, 1H), 8.23 (s, 1H), 7.32-7.19 (m, 5H), 5.73 (s, 2H), 5.39 (s, 2H), 4.61 (d, J$_{H-H}$=5.5, 2 H); $^{19}$F NMR (376 MHz, CDCl$_3$) δ −141.70 (dd, $^1J_{F-F}$=23.2, $^2J_{F-F}$=7.2 Hz, ortho-fluorines), −152.7 (t, J$_{F-F}$=22 Hz, para-fluorine), —161.43 (dt, $^1J_{F-F}$=22.9, $^2J_{F-F}$=7.4 Hz, meta-fluorines); $^{13}$C NMR (100 MHz, DMSO) δ 155.5 (s), 153.8 (s), 150.3 (s), 145.6 (dm, $^1J_{C-F}$=254 Hz), 143.14 (s), 142.01 (d, $^1J_{C-H}$=199 Hz), 141.6 (dm, $^1J_{C-F}$=259 Hz), 137.7 (d, $^1J_{C-F}$=249 Hz), 139.9 (s), 128.9 (dd, $^1J_{C-H}$=159 Hz, $^2J_{C-H}$=6 Hz), 127.9 (dm, $^1J_{C-H}$=154 Hz), 127.5 (d, $^1J_{C-H}$=164 Hz), 124.8 (d, $^1J_{C-H}$=197 Hz,), 118.8 (s), 109.8 (t, $^2J_{C-F}$=18 Hz), 43.8 (t, $^1J_{C-H}$=139 Hz,), 41.1 (t, $^1J_{C-H}$=130 Hz), 38.8 (t, $^1J_{C-H}$=142 Hz).

Results

Synthesis

Referring to scheme 1, described previously, the triazole, 6, and its fluorinated derivatives, compounds 7-9, were prepared by the Sharpless-Huisgen's Cu(I) catalyzed 1,3-dipolar cycloaddition reactions of the corresponding alkyne and azide substrates. As expected, the products show high 1,4-regioselectivity in these cycloadditions.

Reaction of the commercially available 2,6-dichloropurine (3) with benzylamine gave 2-chloro-6-benzylaminopurine (4) using a reported procedure. Under our conditions, the reaction was complete in 15 min at 60° C. instead of the reported time of 3 h at 110° C. Propargylation of compound 4 using propargyl bromide in DMSO under mild conditions gave 2-chloro-6-benzylamino-9-(2-propynyl) purine (5) regioselectively in high yield. The Cu(I) catalyzed azide-alkyne click reaction (the Sharpless-Huisgen 1,3-dipolar cycloaddition) of the alkyne 5 with fluorinated benzyl azides, prepared in situ from their corresponding benzyl bromides, gave exclusively 1,4-disubstituted triazoles, 7-9. The isomeric homogeneity of the product triazoles was readily verified through their $^{19}$F NMR spectra. The pentafluorophenyl-methyl-triazole, 9, showed relatively shielded δ$^{19}$F absorptions as compared to the o-fluorophenylmethyl- and the 2,6-difluorophenylmethyl-triazoles, 7 and 8 respectively, in accordance with similar observations for the monofluoro-, difluoro-, and pentafluorotoluenes.

Aβ has been known to overactivate CDK5 which results in the tau-hyperphosphorylation, and cell cycle re-entry, leading to neuronal apoptosis. Thus, we used Aβ oligomers as the trigger of neurotoxicity in vitro for convenient assay of the neuroprotective effects of the kinase inhibitors.

Figure 2:
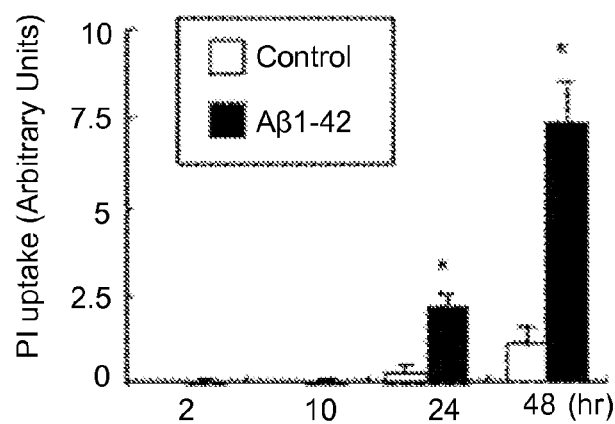
FIG. 2 illustrates a chart showing PI uptake responses between groups.

Mouse hippocampal slice cultures were treated with Aβ oligomers in the presence of PI as the staining agent. The degree of hippocampal neuronal death was monitored by fluorescence microscopic observation of the PI uptake. The intensities of the fluorescence were conveniently analyzed using Scion images. The intensity of the PI fluorescence reflects the relative number of the dead cells, since PI cannot permeate the live cell membranes. As shown in FIGS. 1-2, there is visible difference in the control (in the absence of Aβ oligomers) and the Aβ oligomers-treated cell cultures. Typically 48 h is required for the expression of the Aβ toxicity.

These experiments were repeated using the established cell cycle inhibitors, Roscovitine, Flavopiridol, and the triazoles, 6, 7, 8, and 9.

Figure 3:
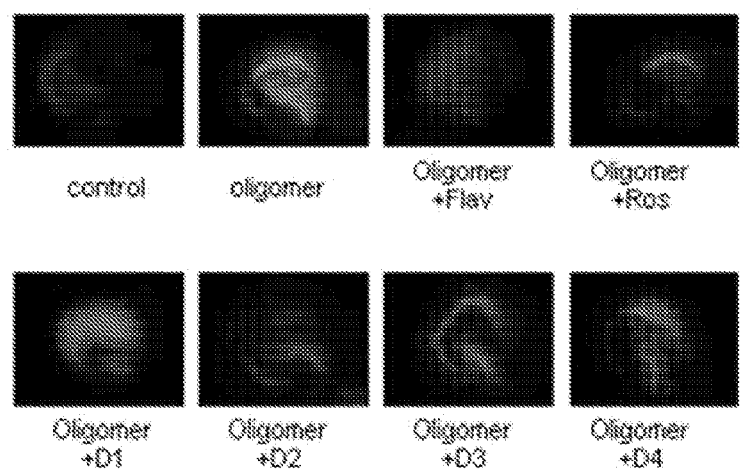
FIG. 3 illustrates fluorescence microscopy images showing the relative PI uptake in hippocampal slices incubated with various compounds (1 μM; 1 h) followed by Aβ oligomers (5 μM; 48 h).
Figure 4:
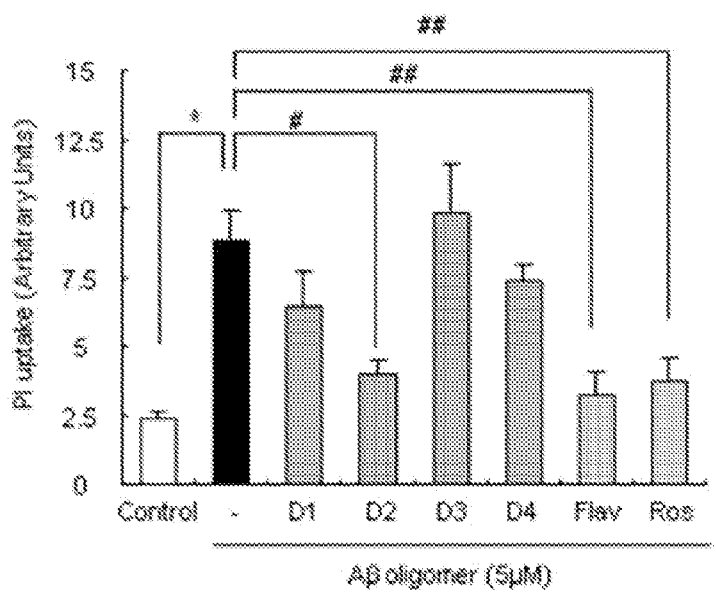
FIG. 4 illustrates a chart showing PI uptake responses. Data were expressed as the means±S.E. (n=4). Differences between groups were examined for statistical significance using one-way analysis of variance with an unpaired Students t-test (*: $p<0.05$; #: $p<0.05$, ##: $p<0.01$).

As can be seen in FIGS. 3-4, after 48 h of incubation time, Roscovitine, Flavopiridol and the o-fluorophenylmethyl-triazole, compound 7, have neuronal cell survival rates comparable to those of the control experiments, i.e., those corresponding to the cultures in the absence of the Aβ oligomers. Interestingly, the pentafluorophenylmethyl-triazole (9) has virtually no neuroprotective effect, and the 2,6-difluorophenylmethyl-triazole (8) and the nonfluorinated-analogue (6) have only marginal effects. Thus the degree of fluorination has a dramatic effect on the neuroprotective effects of these compounds, implying that these compounds may serve as substrates for CDK5/p25 complex which is responsible for the cell cycle re-entry, eventually leading neuronal cell death.

Figure 5:
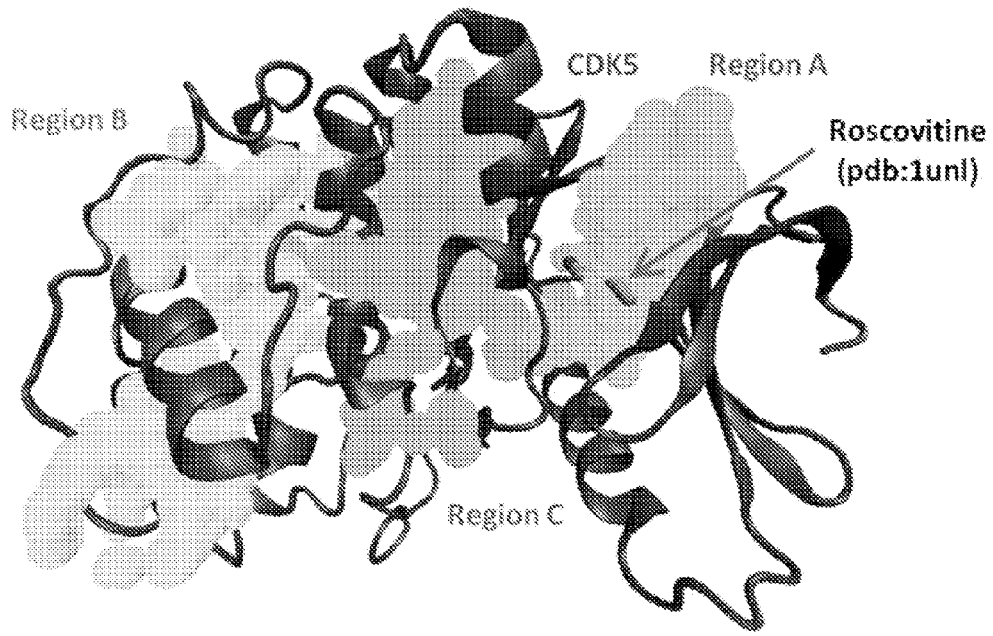
FIG. 5 illustrates a schematic view of potential Roscovitine binding regions in CDK5/p25 obtained from DarwinDock/ GenDock simulations; Region A is the highest scoring site in accordance with co-crystal structure, 1UNL.
Figure 6:
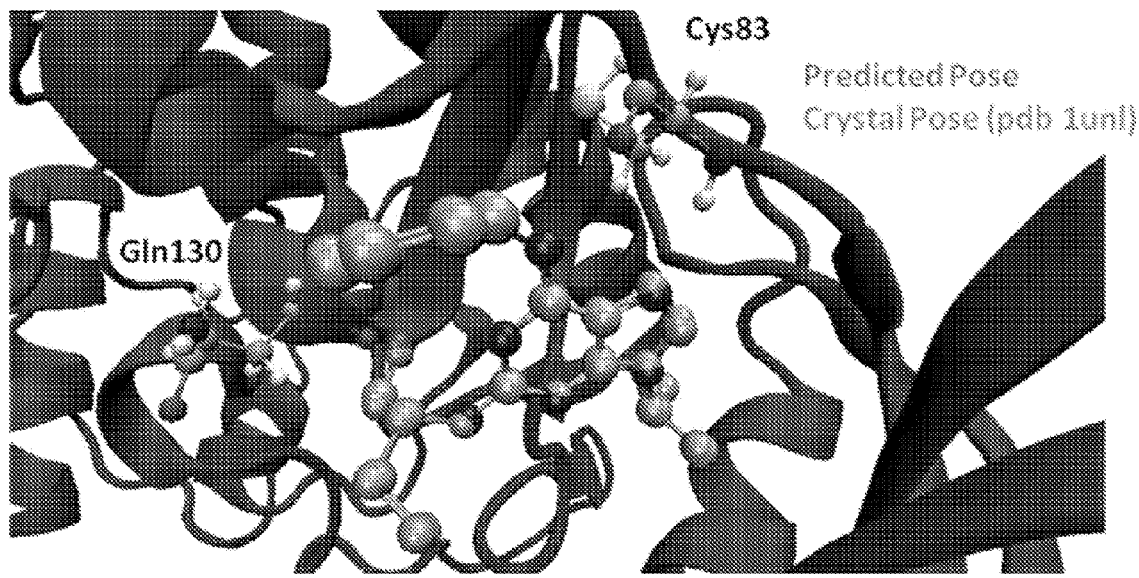
FIG. 6 illustrates an expanded view of the Roscovitine-CDK5/p25 complex showing the x-ray structure (1UNL) superimposed on the DarwinDock/GenDock simulated structure.

The neurotoxicity of Aβ peptide may arise primarily due to its overactivation of CDK5/p25 complex followed by cell cycle re-entry. Thus, selective enzyme inhibitors for CDK5/p25 are the ideal target for designing state of the art neuroprotective agents. Goddard's state of the art molecular docking methods, DarwinDock/GenDock, are ideally suited in the design of these selective inhibitors. We have shown the validity of these calculations for CDK5/p25 by reproducing the Roscovitine/CDK5-p25 cocrystal structure from protein data bank (PDB; 1UNL). We have located three potential binding regions (A, B, and C; FIGS. 5-6) in CDK5/p25 and showed that all high scoring poses preferred Region A which is consistent with the binding site observed in the co-crystal, 1UNL. In addition, the binding pose is within 0.17 A ° (heavy atom RMSD) of the pose observed in the co-crystal structure (1UNL). The predicted structure superimposed on the experimental co-crystal structure (1UNL) is shown in FIG. 4.

Figure 7:
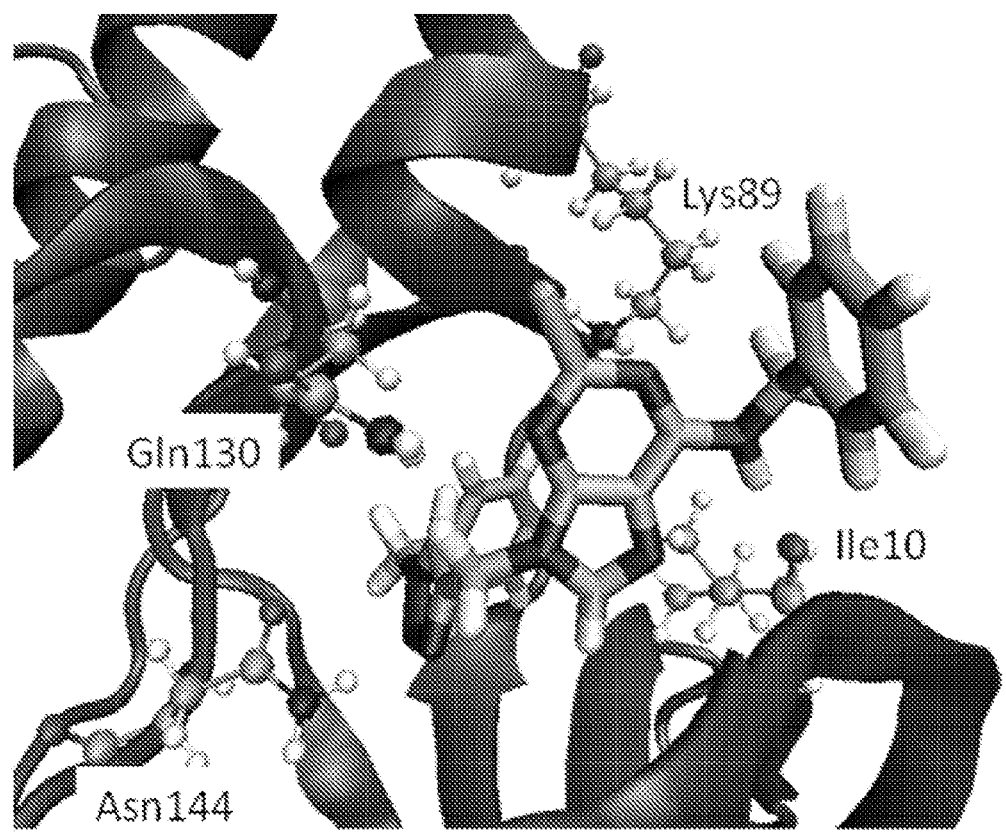
FIG. 7 illustrates an expanded view of the Compound 7-CDK5/p25 complex, showing hydrogen bonds to Lys89, Ile10, Asn144 and Gln130.

Docking of Compounds 7 and 9 to the three potential ligand binding regions predicts that these inhibitors also prefer region A. The closeup view of the binding site for compound 7 is shown in FIG. 7. The later site overlaps the Roscovitine site but the molecule has a different pose and interacts strongly with a different set of CDK5 residues except for Gln130. It shows three strong H-bonding interactions with Asn144, Lys89, backbone carbonyl of Ile10, and relatively weaker interaction with Gln130.

Compound 9 shows the same binding pose as Compound 7, as expected from the structural similarities. The relative binding energies for Roscovitine, and compounds 7 and 9 are −48.1 kcal/mol, −44.8 kcal/mol, and −33.3 kcal/mol, respectively, which correlates well with the PI assay. The similar binding energies for Roscovitine and compound 7 are in accordance with their comparable neuroprotective effects (FIG. 2), whereas the much lower binding energy for the compound 9 is consistent with its ineffectiveness in enzyme binding observed in our experiments (FIG. 2). The difference in binding energies for compounds 7 and 9 comes mainly from the larger desolvation penalty needed to bury the pentafluorophenyl group of Compound 9 as compared to the o-fluorophenyl group of compound 7. This desolvation penalty difference, calculated using an implicit solvation model (Poisson-Boltzmann), is about 9 kcal/mol and accounts for most of the reduction in binding energy of compound 9.

In summary, we have found that our o-fluorophenylmethyl derived triazole, 7, effectively suppressed Aβ-induced neurotoxicity in hippocampal slice cultures, while the pentafluoroaryl derived triazole 9 has virtually no neuroprotective effect Importantly, the neuroprotective effect of compound 7 is comparable to Flavopiridol and Roscovitine, state of the art pharmaceuticals. These results suggest our newly synthesized compound 7 as a therapeutic candidate for AD and other neurological disorders. Indeed, DarwinDock/GenDock docking calculations show that the Roscovitine and the triazoles 7 and 9 all bind at the same active site region of the CDK5/p25 complex, with relative binding affinities of −48.1 kcal/mol, −44.8 kcal/mol, and −33.3 kcal/mol, respectively. The comparable neuroprotective effects of Roscovitine and compound 7 are thus reflected in their similar binding affinities, whereas the unfavorably low binding affinity for compound 7 makes it practically inefficient neuroprotector. These docking simulations also support the involvement of the CDK5/p-25 complex in the cell cycle re-entry, a leading cause of the neuronal degeneration.

From the above description of the invention, those skilled in the art will perceive improvements, changes and modifications. Such improvements, changes, and modifications are within the skill of the art and are intended to be covered by the appended claims. All patents and publications identified herein are incorporated by reference in their entirety.

Having described the invention, the following is claimed:

1. A compound of formula I

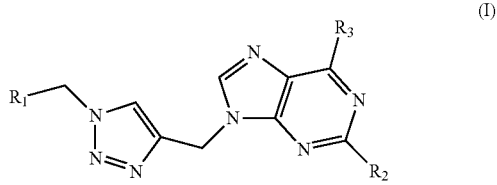

or a pharmaceutically acceptable salt thereof, where $R_1$ is a hydrophobic, substituted or unsubstituted, aryl, cyclic, or heterocyclic group;

where $R_2$ and $R_3$ independently represent substituents selected from the group consisting of hydrogen, halogen, $C_1$-$C_{24}$ alkyl, $C_2$-$C_{24}$ alkenyl, $C_2$-$C_{24}$ alkynyl, $C_3$-$C_{20}$ aryl, $C_6$-$C_{24}$ alkaryl, $C_6$-$C_{24}$ aralkyl, silyl, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, $C_2$-$C_{24}$ alkylcarbonyl (—CO-alkyl), $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—NH$_2$), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_1$-$C_{24}$ alkyl)$_2$), mono-substituted arylcarbamoyl (—(CO)—NH-aryl), thiocarbamoyl (—(CS)—NH$_2$), carbamido (—NH—(CO)—NH$_2$), cyano(—CN), isocyano (—NC), cyanato (—O—CN), isocyanato (O—NC), isothiocyanato (—S—NC), azido (—N=N$^+$=N$^-$), formyl (—(CO)—H), thioformyl (—(CS)—H), amino (—NH$_2$), mono- and di-($C_1$-$C_{24}$ alkyl)-substituted amino, mono- and di-($C_5$-$C_{20}$ aryl)-substituted amino, $C_2$-$C_{24}$ alkylamido (—NH—(CO)-alkyl), $C_6$-$C_{20}$ arylamido (—NH—(CO)-aryl), imino, alkylimino, arylimino, nitro (—NO$_2$), nitroso (—NO), sulfonic acid (—SO$_2$—OH), sulfonato (—SO$_2$—O$^-$), $C_1$-$C_{24}$ alkylsulfanyl (—S-alkyl), arylsulfanyl, $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), phosphono (—P(O)(OH)$_2$), phosphonato (—P(O)(O—)$_2$), phosphinato (—P(O)(O$^-$)), phospho (—PO$_2$), and phosphino (—PH$_2$), and where each R$_2$ and R$_3$ being independently unsubstituted or substituted where appropriate by one or more —OH, halogen, amino or alkyl groups.

2. The compound of claim 1, where R1 is a fluorinated aryl, cyclic, or heterocyclic group.

3. The compound of claim 1, where R$_2$ and R$_3$ are each independently a hydrogen, a halogen, C$_1$-C$_{24}$ alkyl, C$_2$-C$_{24}$ alkenyl, C$_2$-C$_{24}$ alkynyl, C$_3$-C$_{20}$ aryl, C$_6$-C$_{24}$ alkaryl, C$_6$-C$_{24}$ aralkyl, or an R$_4$—NH—, R$_4$—NH—NH—, NH$_2$—R'—NH— or R$_4$—NH—R'—NH— radical, in which R$_4$ represents a straight- or branched-chain, saturated or unsaturated alkyl radical, an aryl or cycloalkyl radical or a heterocyclic ring and R' represents a straight- or branched-chain, saturated or unsaturated alkylene group or an arylene or cycloalkylene group, R4 and R' each containing 1 to 8 carbon atoms, and where each R$_2$ and R$_3$ being independently unsubstituted or substituted, where appropriate, by one or more —OH, halogen, amino or alkyl groups.

4. The compound of claim 1 having the formula (II):

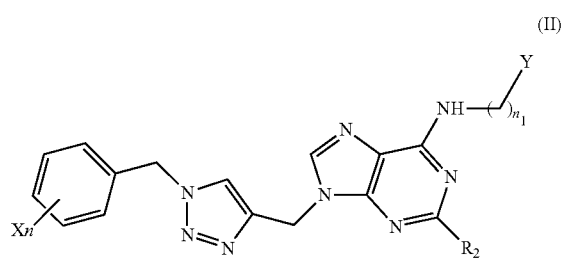

(II)

or a pharmaceutically acceptable salt thereof,
where X is a halogen;
where n is an integer from 0-5;
where n$_1$ is an integer from 1-3;
where Y is substituted or unsubstituted C$_1$-C$_{24}$ alkyl, C$_2$-C$_{24}$ alkenyl, C$_2$-C$_{24}$ alkynyl, C$_3$-C$_{20}$ aryl, C$_6$-C$_{24}$ alkaryl, C$_6$-C$_{24}$ aralky; and
where R$_2$ is a hydrogen, a halogen, C$_1$-C$_{24}$ alkyl, C$_2$-C$_{24}$ alkenyl, C$_2$-C$_{24}$ alkynyl, C$_3$-C$_{20}$ aryl, C$_6$-C$_{24}$ alkaryl, C$_6$-C$_{24}$ aralkyl, or an R$_4$—NH—, R$_4$—NH—NH—, NH$_2$—R'—NH— or R$_4$—NH—R'—NH— radical, in which R$_4$ represents a straight- or branched-chain, saturated or unsaturated alkyl radical, an aryl or cycloalkyl radical or a heterocyclic ring and R' represents a straight- or branched-chain, saturated or unsaturated alkylene group or an arylene or cycloalkylene group, R$_4$ and R' each containing 1 to 8 carbon atoms, and where R$_2$ is unsubstituted or substituted, where appropriate, by one or more —OH, halogen, amino or alkyl groups. In one example, R$_2$ is hydrogen, Cl, F, an alkyl or substituted alkyl.

5. The compound of claim 1, having the formula (III)

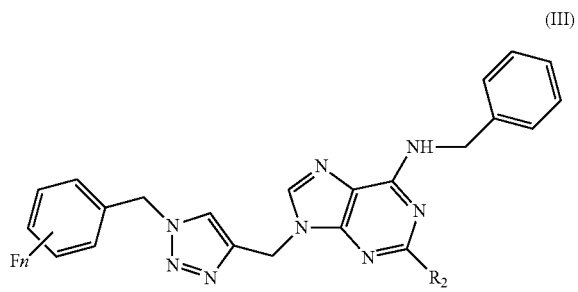

(III)

or a pharmaceutically acceptable salt thereof,
where n is an integer from 0-5; and ortho-, meta- and para-isomers,
where R$_2$ is a hydrogen, a halogen, C$_1$-C$_{24}$ alkyl, C$_2$-C$_{24}$ alkenyl, C$_2$-C$_{24}$ alkynyl, C$_3$-C$_{20}$ aryl, C$_6$-C$_{24}$ alkaryl, C$_6$-C$_{24}$ aralkyl, or an R$_4$—NH—, R$_4$—NH—NH—, NH$_2$—R'—NH— or R$_4$—NH—R'—NH— radical, in which R$_4$ represents a straight- or branched-chain, saturated or unsaturated alkyl radical, an aryl or cycloalkyl radical or a heterocyclic ring and R' represents a straight- or branched-chain, saturated or unsaturated alkylene group or an arylene or cycloalkylene group, R$_4$ and R' each containing 1 to 8 carbon atoms, and where R$_2$ is unsubstituted or substituted, where appropriate, by one or more —OH, halogen, amino or alkyl groups.

6. The compound of claim 1, where R2 is Cl, F, an alkyl or substituted alkyl.

7. A pharmaceutical composition comprising a compound according to claim 1, admixed with a pharmaceutically acceptable diluent, excipient, carrier or mixtures thereof.

8. A method for promoting neuron survival in the presence of amyloid β, the method comprising:
   administering to a neuron in the presence of amyloid β a therapeutically effective amount of a compound according to claim 1.

9. A method for treating a neurological disorder wherein the neurological disorder is Alzheimer's disease in a subject, the method comprising:
   administering to the subject a therapeutically effective amount of a compound according claim 1, and a pharmaceutical carrier.

10. The method of claim 9, the neurological disorder being mediated by amyloid β.

11. The method of claim 9, the compound being administered at an amount effective to promote neuronal survival.

\* \* \* \* \*

UNITED STATES PATENT AND TRADEMARK OFFICE
CERTIFICATE OF CORRECTION

| | |
|---|---|
| PATENT NO. | : 8,969,556 B2 |
| APPLICATION NO. | : 13/879101 |
| DATED | : March 3, 2015 |
| INVENTOR(S) | : Prakash V. Reddy et al. |

It is certified that error appears in the above-identified patent and that said Letters Patent is hereby corrected as shown below:

Title Page:

(73) Assignee: should be --Case Western Reserve University, Cleveland, OH and The Curators of the University of Missouri, Columbia, MO--

Signed and Sealed this
Twenty-sixth Day of April, 2016

Michelle K. Lee
*Director of the United States Patent and Trademark Office*